United States Patent
Toporek et al.

(10) Patent No.: US 12,096,993 B2
(45) Date of Patent: Sep. 24, 2024

(54) FEEDBACK CONTINUOUS POSITIONING CONTROL OF END-EFFECTORS

(71) Applicant: KONINKLIJKE PHILIPS N.V., Eindhoven (NL)

(72) Inventors: Grzegorz Andrzej Toporek, Cambridge, MA (US); Marcin Arkadiusz Balicki, Cambridge, MA (US); Aleksandra Popovic, Boston, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 470 days.

(21) Appl. No.: 17/434,734

(22) PCT Filed: Feb. 21, 2020

(86) PCT No.: PCT/EP2020/054576
§ 371 (c)(1),
(2) Date: Aug. 28, 2021

(87) PCT Pub. No.: WO2020/173815
PCT Pub. Date: Sep. 3, 2020

(65) Prior Publication Data
US 2022/0125530 A1    Apr. 28, 2022

Related U.S. Application Data

(60) Provisional application No. 62/825,914, filed on Mar. 29, 2019, provisional application No. 62/825,905, (Continued)

(51) Int. Cl.
A61B 34/20    (2016.01)
A61B 8/12     (2006.01)
(Continued)

(52) U.S. Cl.
CPC ............. *A61B 34/20* (2016.02); *A61B 8/12* (2013.01); *A61B 34/30* (2016.02); *A61B 90/37* (2016.02);
(Continued)

(58) Field of Classification Search
CPC .......... A61B 34/20; A61B 34/30; A61B 8/12; A61B 90/37; A61B 2034/107;
(Continued)

(56) References Cited

U.S. PATENT DOCUMENTS 5,579,442 A  * 11/1996 Kimoto ............... B25J 9/161
                                                    700/251
8,348,861 B2    1/2013 Glozman et al.
(Continued)

FOREIGN PATENT DOCUMENTS

CN    101222882 A    7/2008
CN    105078576 A    11/2015
(Continued)

OTHER PUBLICATIONS

International Search Report and Written Opinion of PCT/EP020/054576, dated May 29, 2020.
(Continued)

*Primary Examiner* — Sean D Mattson

(57) ABSTRACT

A positioning controller (50) including an imaging predictive model (80) and inverse control predictive model (70). In operation, the controller (50) applies the imaging predictive model (80) to imaging data generated by an imaging device (40) to render a predicted navigated pose of the imaging device (40), and applies the control predictive model (70) to error positioning data derived from a differential aspect between a target pose of the imaging device (40) and the predicted navigated pose of the imaging device (40) to render a predicted corrective positioning motion of the
(Continued)

imaging device (40) (or a portion of the interventional device associated with this imaging device) to the target pose. From the predictions, the controller (50) further generates continuous positioning commands controlling a corrective positioning by the interventional device (30) of the imaging device (40) (or said portion of interventional device) to the target pose based on the predicted corrective positioning motion of the interventional device (30).

20 Claims, 25 Drawing Sheets

Related U.S. Application Data filed on Mar. 29, 2019, provisional application No. 62/811,705, filed on Feb. 28, 2019.

(51) Int. Cl.
| | |
|---|---|
| A61B 34/30 | (2016.01) |
| A61B 90/00 | (2016.01) |
| B25J 9/16 | (2006.01) |
| G06N 3/044 | (2023.01) |
| G06N 3/045 | (2023.01) |
| G06N 3/047 | (2023.01) |
| G06N 3/08 | (2023.01) |
| G06N 3/084 | (2023.01) |
| G06T 7/246 | (2017.01) |
| G06T 7/70 | (2017.01) |
| G16H 20/40 | (2018.01) |
| G16H 30/20 | (2018.01) |
| A61B 34/10 | (2016.01) |

(52) U.S. Cl.
CPC .......... *B25J 9/1607* (2013.01); *B25J 9/1697* (2013.01); *G06N 3/044* (2023.01); *G06N 3/045* (2023.01); *G06N 3/047* (2023.01); *G06N 3/08* (2013.01); *G06N 3/084* (2013.01); *G06T 7/246* (2017.01); *G06T 7/70* (2017.01); *G16H 20/40* (2018.01); *G16H 30/20* (2018.01); *A61B 2034/107* (2016.02); *A61B 2034/2061* (2016.02); *A61B 2034/2065* (2016.02); *A61B 2034/301* (2016.02); *A61B 2090/378* (2016.02); *G06T 2207/20084* (2013.01); *G06T 2207/30244* (2013.01)

(58) Field of Classification Search
CPC .... A61B 2034/2061; A61B 2034/2065; A61B 2034/301; A61B 2090/378; A61B 2090/064; B25J 9/1607; B25J 9/1697; G06N 3/044; G06N 3/045; G06N 3/047; G06N 3/08; G06N 3/084; G06N 3/048; G06N 3/082; G06T 7/246; G06T 7/70; G06T 2207/20084; G06T 2207/30244; G16H 20/40; G16H 30/20; G05B 19/423; G05B 2219/39286

See application file for complete search history.

(56) References Cited

U.S. PATENT DOCUMENTS

| | | | |
|---|---|---|---|
| 2006/0258938 A1* | 11/2006 | Hoffman | A61B 5/06 600/424 |
| 2009/0088634 A1* | 4/2009 | Zhao | A61B 1/00193 600/425 |
| 2012/0158179 A1* | 6/2012 | Ooga | B25J 9/1697 901/47 |
| 2015/0320514 A1* | 11/2015 | Ahn | A61B 34/30 606/130 |
| 2016/0338667 A1 | 11/2016 | Noonan | |
| 2017/0143429 A1* | 5/2017 | Richmond | A61B 34/37 |
| 2017/0312039 A1 | 11/2017 | Crawford | |
| 2017/0334066 A1* | 11/2017 | Levine | G06N 3/045 |
| 2018/0055577 A1 | 3/2018 | Barral | |
| 2018/0110573 A1 | 4/2018 | Kostrzewski | |
| 2018/0158209 A1 | 6/2018 | Fine | |
| 2018/0078318 A1 | 11/2018 | Barbagli | |
| 2020/0261155 A1 | 8/2020 | Popovic et al. | |
| 2021/0015453 A1 | 1/2021 | Toporek | |

FOREIGN PATENT DOCUMENTS

| | | | | |
|---|---|---|---|---|
| EP | 2942029 A1 | 11/2015 | | |
| JP | 2015213753 A | 12/2015 | | |
| WO | 2018002109 A1 | 1/2018 | | |
| WO | WO-2018045551 A1 * | 3/2018 | | G06N 3/08 |

OTHER PUBLICATIONS

Thomas, George Thuruthel et al "Learning Closed Loop Kinematic Controllers for Continuum Manipulators in Unstructured Environments", Soft Robotics, vol. 4, No. 3, 2017.

Xu, Wenjun et al "Data-driven Methods towards Learning the Highly Nonlinear Inverse Kinematics of Tendon-Driven Surgical Manipulators", International Journal of Medical Robotics Comput. Assist. Surgery, 2016.

Braganza, David et al "A Neural Network Controller for Continuum Robots" IEEE Transactions on Robotics, vol. 32, No. 5, Dec. 2007.

Falkenhahn, Valentin Ete Al "Model-based Feedforward Position Control of Constant Curvature Continuum Robots using Feedback Linearization", IEEE International Conf. on Robotics and Automation, 2016.

* cited by examiner

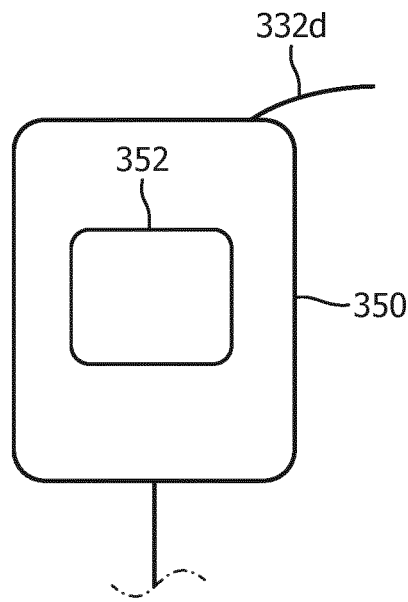
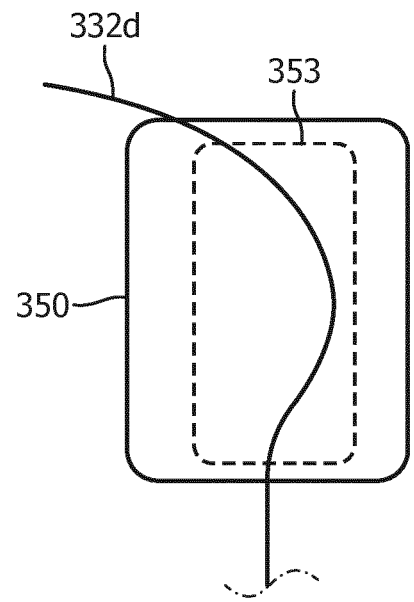
FIG. 16A            FIG. 16B
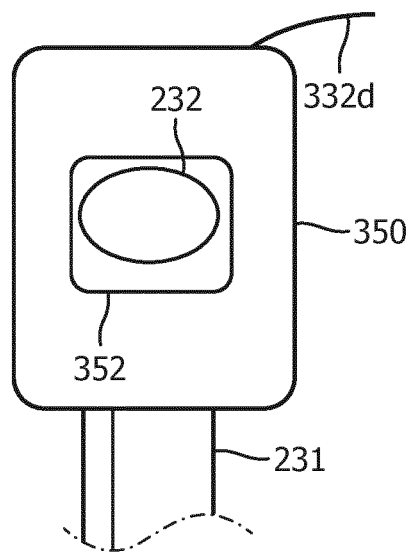
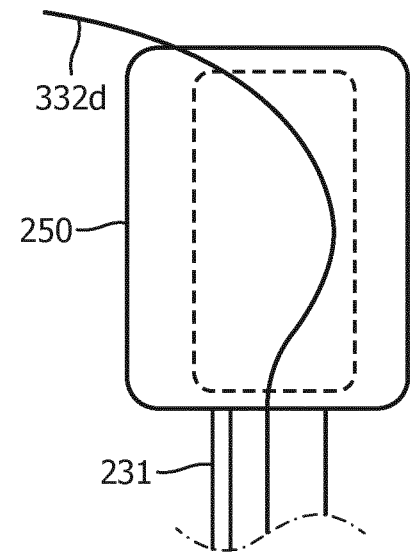
FIG. 16C            FIG. 16D

FEEDBACK CONTINUOUS POSITIONING CONTROL OF END-EFFECTORS

FIELD OF THE INVENTION

The present disclosure generally relates to a positioning control of portions of interventional devices (e.g. end-effectors of interventional devices) utilized in interventional procedures (e.g., minimally-invasive surgery, video-assisted thoracic surgery, vascular procedures, endoluminal procedures, orthopedic procedures). The present disclosure can specifically relate to incorporation of predictive models in the positioning control of such portions of interventional devices utilized in interventional procedures.

BACKGROUND OF THE INVENTION

Continuous (or non-continuous) control—positioning of said device portion (e.g. end-effector) within a certain workspace—is one of the most commonly attempted forms of control in conventional rigid link robots. By taking the advantage of a discrete rigid link structure of the robot, a precise positioning of said portion of interventional device (e.g. end-effector) can be achieved as desired in structured applications such as manufacturing. However, usage of rigid link robots in clinical settings is less desired due to deformable, delicate nature of the soft-tissue human organs as well as patient safety.

More particularly, robots that are biologically inspired may produce motion similar to snakes, elephants, and octopuses, which could be a very effective in manipulation of soft anatomical objects. Nonetheless, effective control, and especially effective continuous control, of robotic structures in clinical settings has proven extremely difficult to achieve in view of a complexity in continuum (or quasi-continuum) structures for a desired degrees of freedom being hard to either model mathematically or provide sufficient actuator inputs to enable consistent control.

For example, one approach for continuous positioning control of an end-effector supported by a continuum robot involves a modelling and controlling of a configuration of the continuum robot whereby a static model, which is formulated as a set of nonlinear differential equations, attempts to account for lance deformation of the continuum robot due to bending, torsion, and elongation. However, the accuracy of mathematical modelling is susceptible to changes in the environmental conditions of the robot (e.g., temperature and humidity), which will influence mechanical properties of the robot components, and susceptible to a presence of any manufacturing inaccuracies or various working loads.

By further example, another approach for positioning control of an end-effector supported by a robot a manipulation of the robot by projecting a set of allowable motions and a set of allowable forces into the joint space corresponding to a manipulator control. For instance, after insertion of the robot into a nasal cavity, the controller adjusts the position of each segment of the robot to increase the difference between a measured generalized force and an expected generalized force on each end disk. However, the increased degree-of-freedom of the robot to become more maneuverable has the adverse effect of complicating the kinematics for the robot. This may be particularly problematic in case of continuous control of a continuum robot.

Moreover, even if effective positioning control of an end-effector supported by a robot is achieved, an incorrect calibration or usage of the robotic system or general wear and tear of the mechanical components may however negatively influence the prediction accuracy of the kinematics of the robotic structure. Again, this may be particularly problematic in case of continuous control of a continuum robot (or continuum robotic structure).

SUMMARY OF THE INVENTION

Known techniques devised for positioning controls of portions of interventional devices (e.g. end-effectors) have provided limited benefits. Thus, there remains a need for improved techniques for providing an effective positioning controls of these portions of interventional devices. To this end, the present disclosure teaches a feed-forward positioning control, a feedback positioning control and a data collection. This control is preferably executed continuously.

To this purpose, the invention proposes as a first embodiment a positioning controller for an interventional device including an imaging device as recited in any of claims 1 to 12.

As a second and third embodiments, the invention proposes a (optionally non-transitory) machine readable storage medium encoded with instructions according to claim 13 and a method of positioning, executable by a positioning controller for an interventional device, according to claim 14.

Feed-Forward (preferably Continuous) Positioning Control. The present disclosure further teaches a predictive model approach for a feed-forward (preferably continuous) positioning control of a manual navigated positioning or an automated navigated positioning of a device portion (e.g. an end-effector) supported by an interventional device based on a predictive model configured with kinematics of the interventional device, optionally trained on these kinematics.

One other embodiment of the present disclosure for a feed-forward (preferably continuous) positioning control of a device portion (e.g. an end-effector) is a (continuous) positioning controller including a forward predictive model configured with (optionally forward) kinematics of the interventional device (optionally trained on these forward kinematics of the interventional device) predictive of a navigated pose of the end-effector and/or an control (optionally inverse) predictive model configured with kinematics of the interventional device, optionally trained on inverse kinematics of the interventional device predictive of a positioning motion of the interventional device, predictive of a positioning motion of the interventional device.

For purposes of the description and purposes of the present disclosure, the term "navigated pose" broadly encompasses a pose of said portion of the interventional device (e.g. an end-effector of the interventional device) upon being navigated via the interventional device to a spatial position during an interventional procedure, and the term "positioning motion" broadly encompasses any movement of the interventional device to navigate this device portion to the spatial position during the interventional procedure.

In operation, the continuous positioning controller applies the forward predictive model to a commanded positioning motion of the interventional device to render a predicted navigated pose of the end-effector, and generates continuous positioning data informative of a positioning by the interventional device of said device portion to a target pose based on the predicted navigated pose of said device portion.

Alternatively, antecedently or concurrently, the (preferably continuous) positioning controller applies the inverse predictive model to the target pose of said portion of the interventional device (e.g. end-effector) to render a predicted positioning motion of the interventional device, and generate (continuous) positioning commands controlling a positioning by the interventional device of said device portion to the target pose based on the predicted positioning motion of the interventional device.

Feedback (preferably Continuous) Positioning Control. The present disclosure further teaches a predictive model approach for a feedback (preferably continuous) positioning control of a manual navigated positioning or an (semi-) automated navigated positioning of an imaging device associated with or attached to the portion of the interventional device (e.g. the end-effector of the interventional device) based on an imaging predictive model configured with kinematics of the interventional device (optionally correlated with image data) to receive imaging data from said imaging device as feedback to the manual navigated positioning or the automated navigated positioning of the imaging device (or of the portion of the interventional device linked to the imaging device—e.g. the end-effector) to a target pose. Said predictive model is or has been optionally trained on images generated by the device portion (e.g. end-effector).

One embodiment of the present disclosure for the feedback (preferably continuous) control positioning of the imaging device (or of the portion of the interventional device linked to the imaging device—e.g. the end-effector) is a continuous positioning controller including an imaging predictive model trained on a correlation of a relative imaging by the end-effector and forward kinematics of the interventional device predictive of a navigated pose of the end-effector. The (continuous) positioning controller further may include an control predictive model configured with kinematics of the interventional device predictive of a corrective positioning motion of the interventional device. Optionally this control predictive model has been or is trained on inverse kinematics of the interventional device to output said predictive of a corrective positioning motion.

For purposes of the description and purposes of the present disclosure, the term "relative imaging" broadly encompasses a generation of an image of the interventional procedure by the end-effector at a given pose relative to a reference image of the interventional procedure.

In operation, subsequent to a navigation of the device portion (e.g. end-effector) to a target pose, the (preferably) continuous positioning controller applies the imaging predictive model to imaging data generated by the end-effector to render a predicted navigated pose of the device portion (e.g. end-effector), applies the control (or in particular inverse) predictive model to error positioning data derived from a differential aspect between the target pose of the end-effector and the predicted navigated pose of the end-effector to render a predicted corrective positioning motion of the interventional device, and generates continuous positioning commands controlling a corrective positioning by the interventional device of the imaging device (40) or of the portion of the interventional device associated with the imaging device (e.g. end-effector) to the target pose based on the predicted corrective positioning motion of the interventional device.

Training Data Collection. Additionally, to facilitate the (optional continuous) positioning control of the manual navigated positioning or the automated navigated positioning of a portion of the interventional device (e.g. end-effector) via the predictive models being invariant to environmental differences (e.g., anatomical differences between patients such as patient size, heart location, etc.), the present disclosure further teaches (optionally training) data collection techniques premised on a navigated positioning of said interventional device portion via a pre-defined data point pattern and a recording of a spatial positioning of the interventional device and a pose of said interventional device portion at each data acquisition point to thereby collect (training) data for the predictive models to infer forward kinematics or inverse kinematics of the interventional device.

One embodiment of the present disclosure for collection of (optionally training) data for predictive models is a (optionally training) data collection system for an interventional device including said portion of interventional device (e.g. an end-effector) and sensors adapted to provide position and/or orientation and/or shape information, at least a part of the sensors (332) being affixed to said interventional device portion (optionally in a fixed shape). Such sensors may comprise marking visible from an imaging system (e.g. X-Ray, MRI system), electromagnetic tracking sensors, transducer sensors and/or optical shape sensing provided by/in an optical fiber.

One particular embodiment of this embodiment is a (optionally training) data collection system for interventional device including a portion of an interventional device (e.g. an end-effector) and an optical shape sensor with a segment of the optical shape sensor being affixed to the end-effector (optionally in a fixed shape).

The (training) data collection system may employ a robot controller, a data acquisition controller, a positioning determination module (or shape sensing controller in the above-mentioned particular embodiment) and a data storage controller.

In operation, the data acquisition controller may command the robot controller to control motion variable(s) of the interventional device in accordance with a pre-defined data point pattern, and the positioning determination module (or shape sensing controller) is configured to determine position information based on position and/or orientation and/or shape information received from sensors so as to output an estimation of a pose of said portion of the interventional device portion and/or an estimation of positioning motion of the interventional device at each data point of the pre-defined data point pattern. Said determined position information is thus retrieved or derived or extracted or received to the purpose of said estimations, optionally based on kinematics or interventional device behavior configuring the positioning determination module. In a particular embodiment, the positioning determination module may derive or received a derived shape data from said position and/or orientation and/or shape information to determine said estimations. In case this positioning determination module is a shape sensing controller (as in the particular embodiment above-mentioned) then it controls a shape sensing of the optical shape sensor including an estimation of a pose of the end-effector and an estimation of positioning motion of the interventional device at each data point of the pre-defined data point pattern.

Said "derivation of shape data from said position and/or orientation and/or shape information" may be implemented according to known technique of deriving shape from the data provided by the "sensors". As an example, the positions tracked by the sensors may give a good indication of the general shape of the segment of the interventional device bearing these sensors, and an algorithm (more or less developed according to the distance between the sensors and of possible shape of this interventional device along this segment) may be developed to derive or reconstruct this shape. A dynamic tracking of this positioning may also give indication about the orientation of the deformations. Sensors may also provide strain information (e.g. Rayleigh or Bragg grating sensors) which can indicate local positioning and orientation of the interventional device from which shape can be derived and reconstructed (known techniques too).

The estimation of the pose of the interventional device portion (e.g. an end-effector) is derived from the at least a part of the sensors affixed to the end-effector (optionally in a fixed shape).

Throughout the robot controller may control a motion variable(s) of the interventional device in accordance with pre-defined data point pattern, the data storage controller may receive a communication from the shape sensing controller of an estimated pose of the end-effector for each data point, may receive a communication from the positioning determination module (or shape sensing controller) of an estimated positioning motion of the interventional device for each data point and may receive a communication from the robot controller of the at least one motion variable of the interventional device for each data point.

In response to the communications, the data storage controller may store a temporal data sequence for the interventional device derived from the estimated pose of the end-effector at each data point, the estimated spatial positioning of the interventional device at each data point and the motion variable(s) of the interventional device at each data point. The temporal data sequence may serve as training data for machine learning models of any type, particularly for the predictive models of the present disclosure.

Additionally, the data acquisition controller may further command the robot controller to control the motion variable(s) of the interventional device in accordance with additional pre-defined data point pattern(s) whereby the data storage controller generates additional temporal data sequences for machine learning models of any type, particularly for the predictive models of the present disclosure.

Also, for purposes of the description and claims of the present disclosure:

(1) terms of the art including, but not limited to, "end-effector", "kinematics", "position", "positioning", "pose", "posing", "motion" and "navigation" are to be interpreted as known in the art of the present disclosure and as exemplary described in the present disclosure;

(2) examples of an end-effector include, but are not limited to, an intraoperative imaging devices, interventional tools/surgical instruments and surgical sutures, as known in the art of the present disclosure and hereinafter conceived;

(3) the term "intraoperative imaging device" broadly encompasses all imaging devices, as known in the art of the present disclosure and hereinafter conceived, for illustrating anatomical objects/regions. Examples of intraoperative imaging devices include, but are not limited to, a transesophageal echocardiography transducer (e.g., X7-2t transducer, Philips), laparoscopic ultrasound transducers (e.g., L10-4lap transducer, Philips), optical cameras and sensing devices (e.g., tissue spectral sensing sensors, ECG electrodes, probes for electrophysiological mapping);

(4) examples of interventional tools/surgical instruments include, but are not limited to, scalpels, cauterizers, ablation devices, needles, forceps, k-wires and associated drivers, endoscopes, awls, screwdrivers, osteotomes, chisels, mallets, curettes, clamps, forceps, periosteomes and j-needles, as known in the art of the present disclosure and hereinafter conceived;

(5) the term "interventional device" broadly encompasses all devices, as known in the art of the present disclosure and hereinafter conceived, for supporting a positioning of end-effector during an application. Examples of an interventional device include, but are not limited to, continuum flexible robots, flexible interventional scopes and guidewires;

(6) examples of flexible robots include, but are not limited to, hyper-redundant robots (e.g., multiple discrete links, serpentine links or concentric tubes), continuous backbone section robot (e.g., cable actuated), tendon-drive robots, gel-like soft robot and fluid filled tube actuated robot, as known in the art of the present disclosure and hereinafter conceived;

(7) examples of flexible interventional scopes include, but are not limited to, an endoscope of a transoesophageal echocardiography (TEE) probe, an endoscope of a intracardiac echocardiography (ICE) probe, a laparoscope and a bronchoscope, as known in the art of the present disclosure and hereinafter conceived;

(8) the term "predictive model" broadly encompasses all types of models, as known in the art of the present disclosure and hereinafter conceived, predictive of navigation variables related to a (optionally) continuous positioning control of portions of interventional device (e.g. end-effectors) in accordance with the present disclosure as exemplary described in the present disclosure. Optionally these predictive models may be configured with kinematics to output this prediction based on positioning dataset. Optionally, the predictive models have been trainable or are trained on kinematics of an interventional device. Examples of predictive models include, but are not limited to, artificial neural networks (e.g., feed-forward convolutional neural networks, recurrent neural networks, long short-term memory networks, autoencoder networks, generative adversarial networks, and many others deep learning neural networks);

(9) the term "controller" broadly encompasses all structural configurations, as understood in the art of the present disclosure and as exemplary described in the present disclosure, of main circuit board or integrated circuit for controlling an application of various inventive principles of the present disclosure as exemplary described in the present disclosure. The structural configuration of the controller may include, but is not limited to, processor(s), computer-usable/computer readable storage medium(s), an operating system, application module(s), peripheral device controller(s), slot(s) and port(s), instructions to control. A controller may be housed within or communicatively linked to a workstation;

(10) the term "application module" broadly encompasses an application incorporated within or accessible by a controller consisting of an electronic circuit (e.g., electronic components and/or hardware) and/or an executable program (e.g., executable software stored on non-transitory (or not) computer readable medium(s) and/or firmware) for executing a specific application; and

(11) the terms "signal", "data" and "command" broadly encompasses all forms of a detectable physical quantity or impulse (e.g., voltage, current, or magnetic field strength) as understood in the art of the present disclosure and as exemplary described in the present disclosure for transmitting information and/or instructions in support of applying various inventive principles of the present disclosure as subsequently described in the present disclosure. Signal/data/command communication various components of the present disclosure may involve any communication method as known in the art of the present disclosure including, but not limited to, signal/data/command transmission/reception over any type of wired or wireless datalink and a reading of signal/data/commands uploaded to a computer-usable/computer readable storage medium.

The foregoing embodiments and other embodiments of the present disclosure as well as various structures and advantages of the present disclosure will become further apparent from the following detailed description of various embodiments of the present disclosure read in conjunction with the accompanying drawings. The detailed description and drawings are merely illustrative of the present disclosure rather than limiting, the scope of the present disclosure being defined by the appended claims and equivalents thereof.

BRIEF DESCRIPTION OF THE DRAWINGS

FIG. 15-FIG. 18 illustrate a training data collection system and method of the present disclosure.

DETAILED DESCRIPTION OF THE PREFERRED EMBODIMENTS

The present disclosure is applicable to numerous and various applications that require continuous position control of an end-effector. Examples of such applications include, but are not limited to, minimally-invasive procedures (e.g., endoscopic hepatectomy, necrosectomy, prostatectomy, etc.), video-assisted thoracic surgery (e.g., lobetectomy, etc.), minimally-vascular procedures (e.g., via catheters, sheaths, deployment systems, etc.), minimal medical diagnostic procedures (e.g., endoluminal procedures via endoscopes or bronchoscopes), orthopedic procedures (e.g., via k-wires, screwdrivers, etc.) and non-medical applications.

The present disclosure improves upon continuous position control of an end-effector during such applications by providing a prediction of poses of the end-effector and/or positioning motions of the interventional device that may be utilized to control and/or corroborate a manual navigated positioning or an automated navigated positioning of the end-effector.

Figure 1:
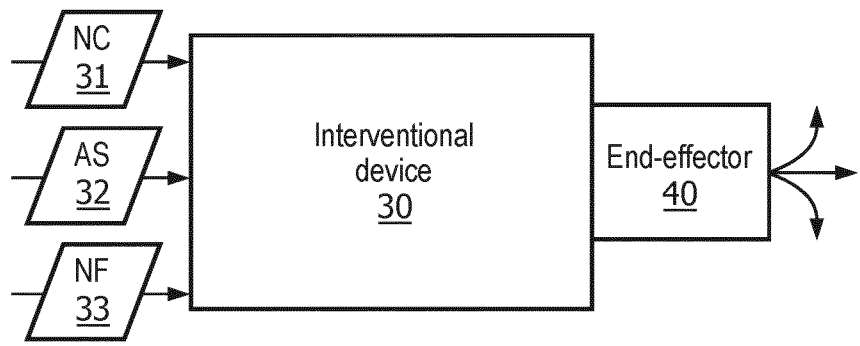
FIG. 1 illustrates an exemplary embodiment of an interventional device including an end-effector as known in the art of the present disclosure.

To facilitate an understanding of the present disclosure, the following description of FIG. 1 teaches exemplary embodiments of an interventional device including an end-effector as known in the art of the present disclosure. From the description of FIG. 1, those having ordinary skill in the art of the present disclosure will appreciate how to apply the present disclosure to make and use additional embodiments of interventional device including an end-effector as known in the art of the present disclosure and hereinafter conceived.

Referring to FIG. 1, in practice, an interventional device 30 supports a manual navigated positioning or an automated navigated positioning of an end-effector 40 during an application as symbolized by the arrows extending from end-effector 40. Examples of interventional device 30 include, but are not limited to, continuum flexible robots, flexible interventional scopes and guidewires, and examples of end-effector 40 include, but are not limited to, intraoperative imaging devices, interventional tools/surgical instruments and surgical sutures.

In operation, navigation command(s) 31, actuation signal(s) 32 and/or navigation force(s) 33 are communicated to/imposed onto interventional device 30 whereby interventional device 30 is translated, rotated and/or pivoted in accordance with the navigation command(s) 31, actuation signal(s) 32 and/or navigation force(s) 33 to thereby navigate end-effector 40 to a target pose (i.e., a location and an orientation in the application space).

Figure 2B:
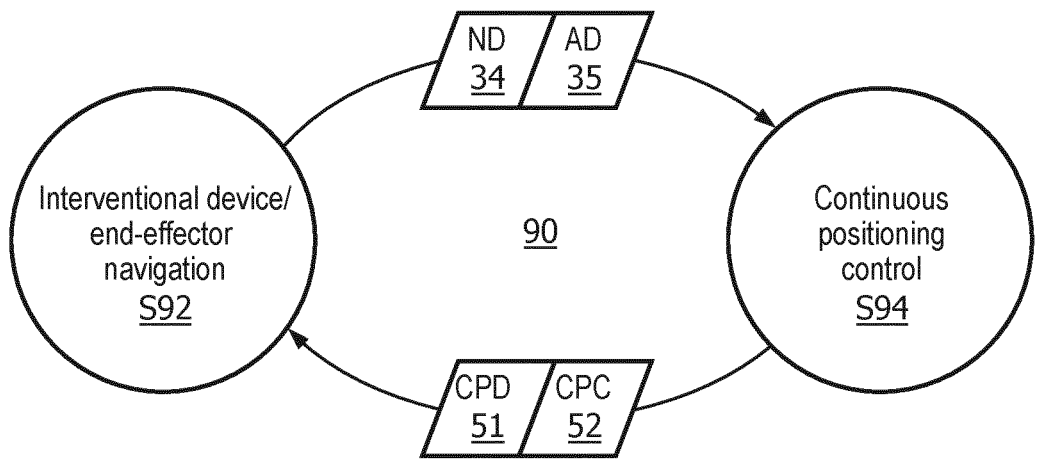
FIG. 2B illustrates an exemplary embodiment of a continuous positioning state machine in accordance with various aspects of the present disclosure.
Figure 3A:
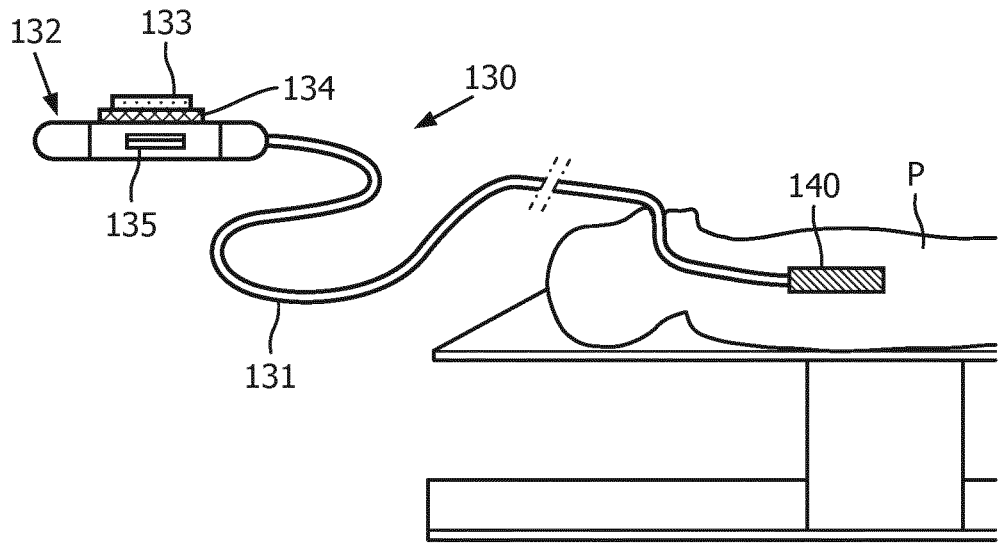
FIG. 3A illustrates an exemplary embodiment of a transesophageal echocardiography (TEE) probe as known in the art of the present disclosure.
Figure 3B:
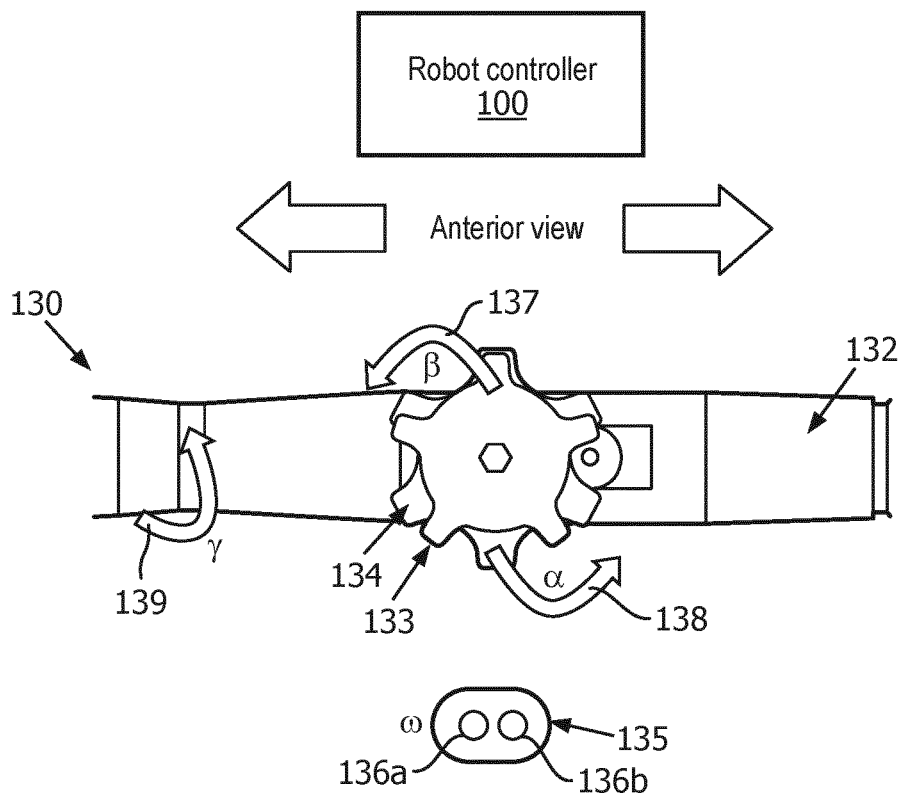
FIG. 3B illustrates an exemplary embodiment of a handle of a transesophageal echocardiography (TEE) probe as known in the art of the present disclosure.

For example, FIGS. 3A and 3B shows a transesophageal echocardiography (TEE) probe 130 as an embodiment of interventional device 30 having an imaging end-effector 140 that is insertable through a mouth of a patient P into an esophagus to capture images of a heart of the patient P, and a practitioner (not shown) or a robot controller 100 (FIG. 2B) operates a handle 132 of TEE probe 130 to reposition TEE probe 130 within patient P to thereby navigate imaging end-effector 140 to a target pose.

More particularly, TEE probe 130 includes flexible elongate member 131, handle 132 and imaging end-effector 140. The flexible elongate member 131 is sized and/or shaped, structurally arranged, and/or otherwise configured to be positioned within a body lumen of a patient, such as an esophagus. The imaging end-effector 140 is mounted at a distal end of the member 131 and includes one or more ultrasound transducer elements whereby imaging end-effector 140 is configured to emit ultrasonic energy towards an anatomy (e.g., the heart) of the patient P. The ultrasonic energy is reflected by the patient's vasculatures and/or tissue structures whereby the ultrasound transducer elements in the imaging end-effector 140 receive the reflected ultrasound echo signals. In some embodiments, the TEE probe 130 may include an internal or integrated processing component that can process the ultrasound echo signals locally to generate image signals representative of the patient P's anatomy under imaging. In practice, the ultrasound transducer element(s) may be arranged to provide two-dimensional (2D) images or three-dimensional (3D) images of the patient P's anatomy. The images acquired by the TEE probe 130 are dependent on the depth of insertion, the rotation, and/or the tilt of the imaging end-effector 140, as described in greater detail herein.

The handle 132 is coupled a proximal end of the member 131. The handle 132 includes control elements for navigating the imaging end-effector 140 to the target pose. As shown, the handle 132 includes knobs 133 and 134, and a switch 135. The knob 133 flexes the member 131 and the imaging end-effector 140 along an anterior-posterior plane of the patient P (e.g., heart). The knob 134 flexes the member 131 and the imaging end-effector 140 along a left-right plane of the patient P. The switch 135 controls beamforming at the imaging end-effector 140 (e.g., adjusting an angle of an imaging plane).

In a manual navigated embodiment, the practitioner manually dials the knobs 133 and 134 and/or manually turns the switch 135 on and/or off as needed to navigate imaging end-effector 140 to the target pose. The practitioner may receive a display of the images generated by imaging end-effector 140 to thereby impose navigation forces 33 (FIG. 1) to control the knobs 133 and 134 and/or the switch 135 on the handle 132.

In an automated navigated embodiment, a robotic system (not shown) may include electrical and/or mechanical components (e.g., motors, rollers, and gears) configured to dial the knobs 133 and 134 and/or turn the switch 135 on and/or off whereby robot controller 100 may receive motion control commands 31 (FIG. 1) from a navigation controller (not shown) or an input device (not shown) to thereby control the knobs 133 and 134 and/or the switch 135 on the handle 132. Alternatively, robot controller 100 may to configured to directly manipulate the TEE probe 130 via actuation signals 32 (FIG. 1) based on a guidance method implemented by robot controller 100.

The TEE probe 130 is maneuverable in various degrees of freedom. FIGS. 3C-3F illustrate various mechanisms for maneuvering the TEE probe 130.

Figure 3C:
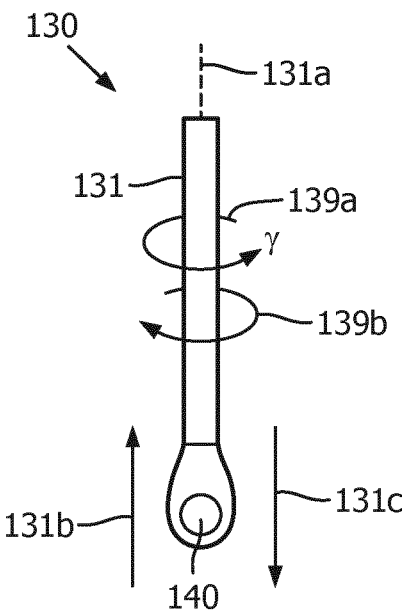
FIGS. 3C-3F illustrate exemplary motions of the TEE probe of FIG. 2A as known in the art of the present disclosure

FIG. 3C is a schematic diagram illustrating TEE probe 130 may be manually advanced into a patient's esophagus as shown by the arrow 131b or withdrawn from the patient's esophagus as shown by the arrow 131c. The TEE probe 130 can be manually or robotically rotated left (e.g., counter-clockwise) or right (e.g., clockwise) with respect to a longitudinal axis 131a of the TEE probe 130 as shown by the arrows 139a and 139b, respectively. The rotations of the member 131 can be described by a parameter, denoted as y.

Figure 3D:
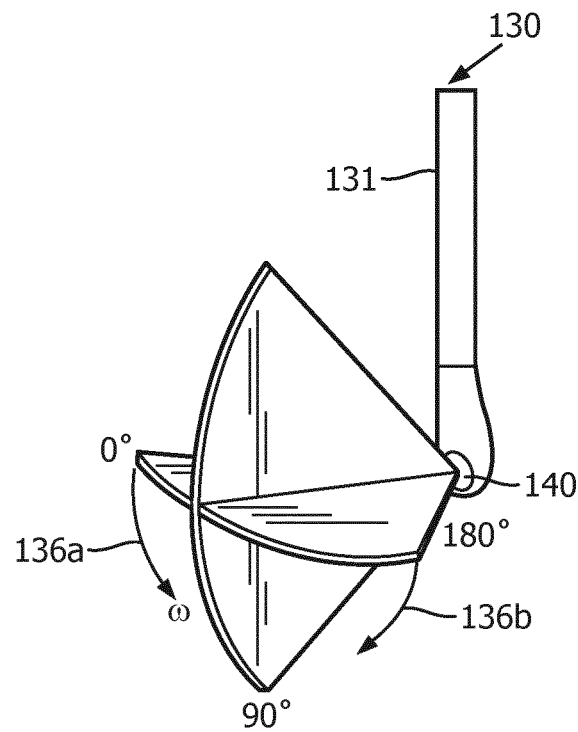

FIG. 3D is a schematic diagram illustrating TEE probe 130 being electronically rotated from 0 degree to 180 degrees (e.g., for beamforming) as shown by the arrows 136a and 136b, for example, by a manual or robotic control of switch 135 on the handle 132. The rotations of the imaging planes can be described by a parameter, denoted as Co.

Figure 3E:
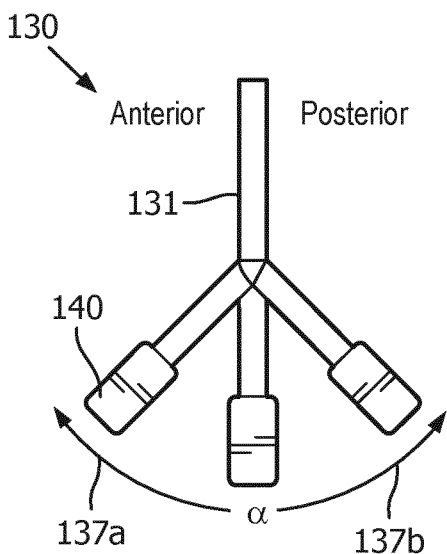

FIG. 3E is a schematic diagram illustrating TEE probe 130 being flexed along an anterior-posterior plane, for example, with respect to a patient's heart, as shown by the arrows 137a and 137b, for example, by a manual or robotic dialing the knob 134 on the handle 132. The flexing along the anterior-posterior plane can be described by a parameter, denoted as u.

Figure 3F:
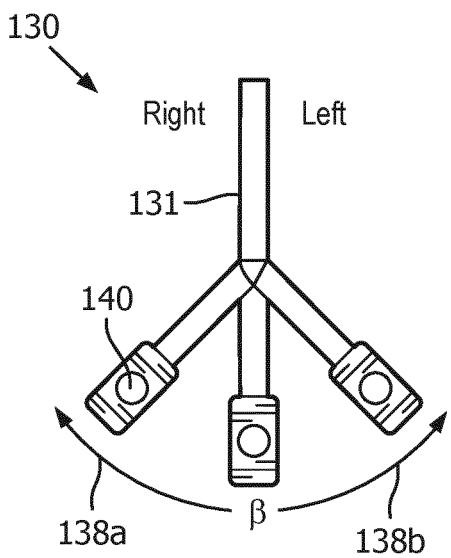

FIG. 3F is a schematic diagram illustrating TEE probe 130 being flexed along a left-right plane, for example, with respect to a patient's heart, as shown by the arrows 138a and 138b, for example, by a manual or robotic dialing the knob 133 on the handle 132. The flexing along the left-right plane can be described by a parameter, denoted as.

Figure 3G:
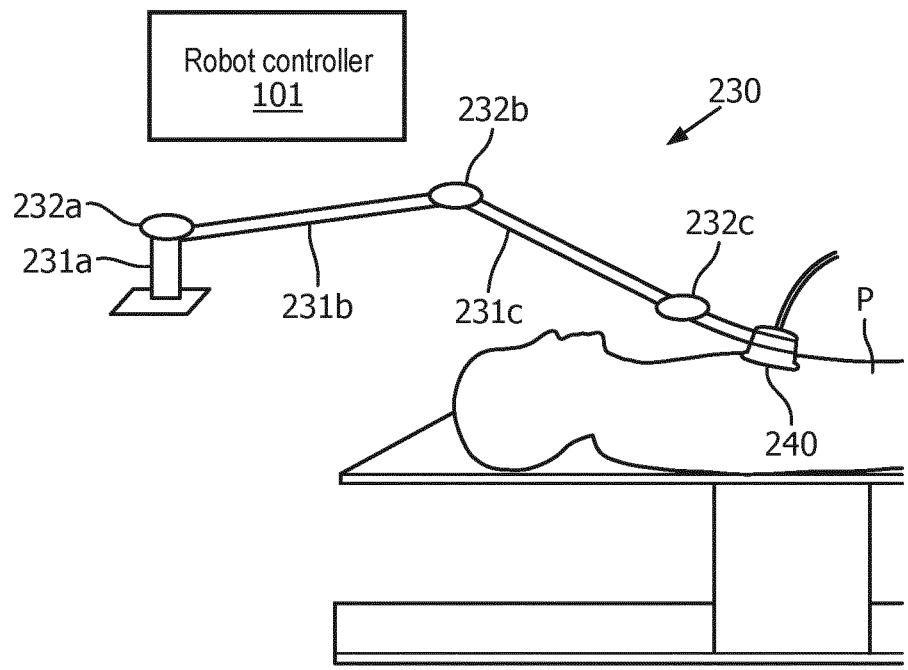
FIG. 3G illustrates an exemplary embodiment of robot manipulated transthoracic echocardiography (TTE) probe as known in the art of the present disclosure.

By further example of an exemplary embodiment of interventional device 30 (FIG. 1), FIG. 3G shows transthoracic echocardiography (TTE) probe 240 configured to capture ultrasound images of an anatomy of patient P from the outside of the body of patient P and a robot 230 as shown for manually or robotically handling TTE probe 240 to reposition the TTE probe 240 to a target pose (i.e., a location and/or an orientation of TTE probe 240 relative to patient P). More particularly, robot 230 includes a plurality of links 231 coupled to a plurality of joints 232 configured to hold the TTE probe 240 and maneuver the TTE probe 240 on an external surface of a patient P (e.g., around the chest area for imaging the heart).

In a manual navigated embodiment, the practitioner manually imposes navigation forces 33 (FIG. 1) onto links(s) 231 to thereby translates, rotates and/or pivots link(s) 231 of robot 230 to navigate imaging TTE probe 240 to the target pose. The practitioner may receive a display of the images generated by TTE probe 240 to utilize as a basis for control of links 231 of robot 230.

In an automated navigated embodiment, a robotic system (not shown) include electrical and/or mechanical components (e.g., motors, rollers, and gears) configured to steer the links 231 of robot 230 whereby robot controller 101 receives motion control commands 32 (FIG. 1) from a navigation controller (not shown) or an input device (not shown) in the form of Cartesian velocity parameters or joint velocity parameters to thereby steer the links 231 of robot 230. Alternatively, robot controller 101 may to configured to directly manipulate the TTE probe 240 via actuation signals 32 (FIG. 1) based on a guidance method implemented by robot controller 101.

Figure 3H:
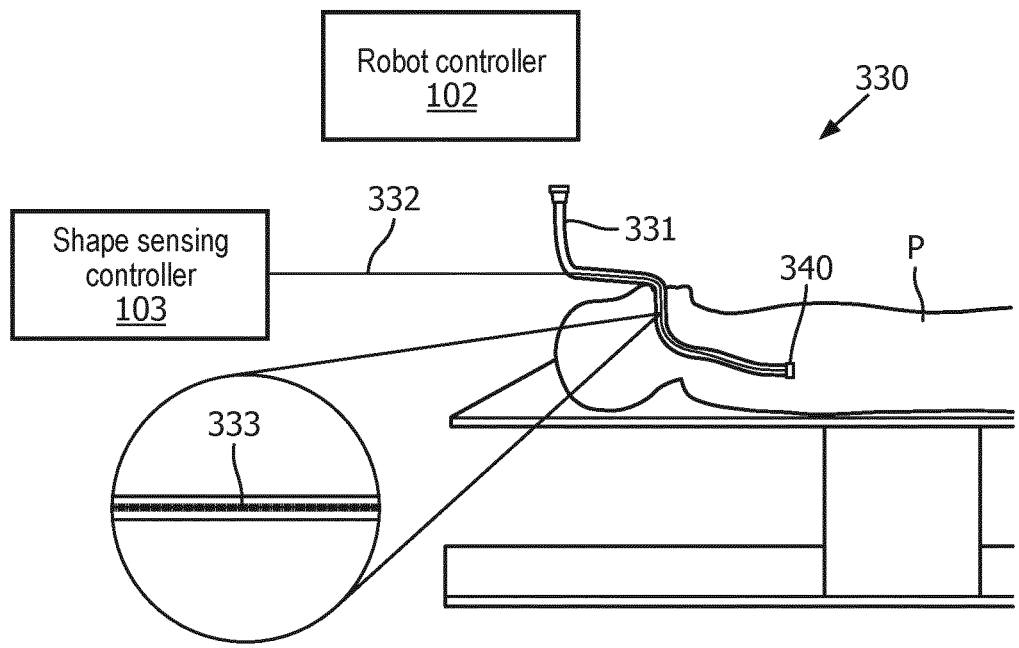
FIG. 3H illustrates an exemplary embodiment of an optical shape sensed continuum robot as known in the art of the present disclosure.

By further example of an exemplary embodiment of interventional device 30 (FIG. 1), FIG. 3H shows a shape-sensed guidewire 332 embedded or attached to a continuum robot 331 having an end-effector 340. The shape-sensed guidewire 232 incorporates optical shape sensing (OSS) technology as known in the art of the present disclosure. More particularly, a shape sensing controller 103 uses light along a multicore optical fiber 333 of guidewire 332 for device localization and navigation during surgical intervention. The principle involved makes use of distributed strain measurements in the optical fiber using characteristic Rayleigh backscatter or controlled grating patterns (e.g. Fiber Bragg Gratings). In practice, shape sensing controller 103 acquires registered shapes of the continuum robot 331 via shape-sensed guidewire 332 as robot controller 102 or a practitioner (not shown) navigates continuum robot 331 within patient P to position end-effector 340 at a target pose.

Figure 2A:
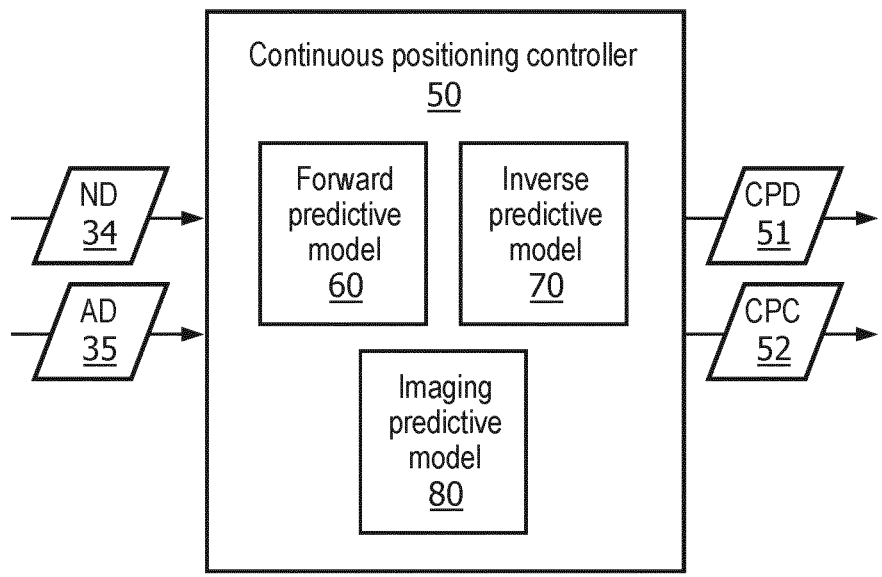
FIG. 2A illustrates an exemplary embodiment of a continuous position controller in accordance with various aspects of the present disclosure.

To further facilitate an understanding of the present disclosure, the following description of FIGS. 2A and 2B teaches exemplary embodiments of a continuous position controller of the present disclosure and a continuous positioning state machine of the present disclosure, respectively. From the description of FIGS. 2A and 2B, those having ordinary skill in the art of the present disclosure will appreciate how to apply the present disclosure to make and use additional embodiments of a continuous position controller of the present disclosure and a continuous positioning state machine of the present disclosure.

Additionally, TEE probe 130 (FIG. 3A), robot 230/TTE probe 240 (FIG. 3G) and continuum robot 331 (FIG. 3H) are utilized herein as non-limiting examples of an interventional device 30 including end-effector 40 (FIG. 1) to support the description of various embodiments of a continuous position controller of the present disclosure. Nonetheless, those having ordinary skill in the art of the present disclosure will appreciate how to apply the present disclosure to various and numerous additional embodiments of interventional device 30 including end-effector 40.

Referring to FIGS. 1, 2A and 2B, interventional device 30 including end-effector 40 and a continuous positioning controller 50 of the present disclosure represent a continuous positioning state machine 90.

Specifically, as shown in FIG. 2B, a state S92 of continuous positioning state machine 90 encompasses a navigation of interventional device 30 including end-effector 40 in accordance with a particular application (e.g., a minimally-invasive procedure, a video-assisted thoracic surgery, a minimally-vascular procedure, a minimally medical diagnostic procedure or an orthopedic procedure). In practice, the application may involve a manual navigation positioning or an automated navigation positioning of the end-effector 40 to a target pose whereby the application incorporates imaging guidance (e.g., image segmentation, image registration, path planning, etc.), interventional device tracking (e.g., electromagnetic, optical or shape sensing), and/or any other navigation technique for positioning end-effector 40 to the target pose.

An execution of state S92 of continuous positioning state machine 90 results in a generation of navigation data 34 and an optional generation of auxiliary data 35. Generally, in practice, navigation data 34 will be in the form of navigation command(s) 31, actuation signal(s) 32 and/or navigation force(s) 33 communicated to/imposed onto interventional device 30, and auxiliary data 35 will be in the form of image(s) of interventional device 30 and/or end-effector 40, operational characteristics of interventional device 30 (e.g., shape, strain, twist, temperature, etc.) and operational characteristics of end-effector 40 (e.g., pose, forces, etc.).

In response thereto, a state S94 of continuous positioning state machine 90 encompasses continuous positioning control by continuous position controller 50 of the navigation of interventional tool 30 and end-effector 40 in accordance with the state S92. To this end, continuous position controller 50 employs a forward predictive model 60 of the present disclosure, an inverse predictive model 70 of the present disclosure and/or an imaging predictive model 80 of the present disclosure.

In practice, as will be further explained in the present disclosure, forward predictive model 60 may be any type of machine learning model or equivalent for a regression of a positioning motion of the interventional device 30 to a navigated pose of end-effector 40 (e.g., a neural network) that is suitable for the particular type of interventional device 30 being utilized in the particular type of application being implemented, whereby forward predictive model 60 is trained on the forward kinematics of interventional device 30 that is predictive of a navigated pose of end-effector 40.

In operation, forward predictive model 60 inputs navigation data 34 (and auxiliary data 35 if communicated) associated with a manual navigation or an automated navigation of interventional device 30 to thereby predict a navigated pose of end-effector 40 corresponding to the navigation of interventional device 30, and outputs continuous positioning data 51 informative of a positioning by interventional device 30 of the end-effector 40 to the target pose based on the predicted navigated pose of end-effector 40. Continuous positioning data 51 may be utilized in state S92 as an control to determine an accuracy and/or execute a recalibration of the manual navigation or the automated navigation of interventional device 30 to position end-effector 40 to the target pose.

In practice, as will be further explained in the present disclosure, inverse predictive model 70 may be any type any type of machine learning model or equivalent for a regression a target pose of end-effector 40 to a positioning motion of the interventional device 30 (e.g., a neural network) that is suitable for the particular type of interventional device 30 being utilized in the particular type of application being implemented, whereby inverse predictive model 60 is trained on the inverse kinematics of interventional device 30 that is predictive of a positioning motion of the interventional device 30.

In operation, inverse predictive model 70 inputs navigation data 34 (and auxiliary data 35 if communicated) associated with a target pose of end-effector 40 to thereby predict a positioning motion of interventional device 30 for positioning end-effector 40 to the target pose, and outputs continuous positioning commands 52 for controlling a positioning by interventional device 30 of end-effector 40 to the target pose based on the predicted positioning motion of interventional device 30. Continuous positioning commands 52 may be utilized in state S92 as a control to execute the manual navigation or the automated navigation of interventional device 30 to position end-effector 40 to the target pose.

In practice, as will be further explained in the present disclosure, imaging predictive model 80 may be any type of machine learning model or equivalent for a regression of relative imaging by the end-effector 40 to a navigated pose of end-effector 40 (e.g., a neural network or a scale invariant feature transform network) that is suitable for the particular type of end-effector 40 being utilized in the particular type of application being implemented, whereby inverse predictive model 60 is trained on a correlation of relative imaging by end-effector 40 and forward kinematics of the interventional device 30 that is predictive of a navigated pose of end-effector 40.

In operation, imaging predictive model 60 inputs auxiliary data 35 in the form of images generated by the end-effector 40 at one or more poses to thereby predict the navigated pose of end-effector 40 as feedback data informative of a corrective positioning by interventional device 30 of the end-effector 40 to a target pose. The feedback data is utilized in a closed loop of state S94 to generate a differential between a target pose of end-effector 40 and the predicted navigated pose of the end-effector 40 whereby inverse predict model 70 may input the differential to predict a corrective positioning motion of interventional device 30 to reposition end-effector 30 to the target pose.

In practice, an embodiment of continuous positioning controller 50 may employ forward predictive model 60, inverse predictive model 70 and/or imaging predictive model 80.

For example, an embodiment of continuous positioning controller 50 may employ only forward predictive model 60 to facilitate a display of an accuracy of a manual navigation or the automated navigation of interventional device 30 to position end-effector 40 to the target pose.

More particularly, a user interface is provided to display an image of an attempted navigation of end-effector 40 to the target pose and an image of the predicted navigated pose of end-effector 40 by forward predictive model 60. A confidence ratio of the prediction is shown to the user. To evaluate prediction uncertainty, multiple feedforward iterations of forward predictive model 60 are performed with dropout enabled stochastically as known in the art of the present disclosure.

By further example, an embodiment of continuous positioning controller 50 may only employ inverse predictive model 70 to command a manual navigation or an automated navigation of interventional device 30 to position end-effector 40 to the target pose.

By further example, an embodiment of continuous positioning controller 50 may only employ imaging predictive model 80 to provide feedback data informative of a corrective positioning by interventional device 30 of the end-effector 40 to a target pose.

By further example, an embodiment of continuous positioning controller 50 may employ forward predictive model 60 and inverse predictive model 70 to thereby command a manual navigation or an automated navigation of interventional device 30 to position end-effector 40 to the target pose and to display of an accuracy of a manual navigation or the automated navigation of interventional device 30 to position end-effector 40 to the target pose.

By further example, an embodiment of continuous positioning controller 50 may employ inverse predictive model 70 and imaging predictive model 80 to thereby command a manual navigation or an automated navigation of interventional device 30 to position end-effector 40 to the target pose and to provide feedback data informative of a corrective positioning by interventional device 30 of the end-effector 40 to the target pose.

To further facilitate an understanding of the present disclosure, the following description of FIGS. 4-14 teaches exemplary embodiments of forward predictive models, inverse predictive models and imaging predictive models of the present disclosure. From the description of FIGS. 4-14, those having ordinary skill in the art of the present disclosure will appreciate how to apply the present disclosure to make and use additional embodiments of forward predictive models, inverse predictive models and imaging predictive models of the present disclosure.

FIGS. 4A-4E illustrate a training and an application of a forward predictive model 60a of the present disclosure trained to forward kinematics of an interventional device 30 (FIG. 1) predictive of a navigated pose of an end-effector 40 (FIG. 1) to thereby, during an interventional procedure, facilitate an application of forward predictive model 60a to a commanded positioning motion of interventional device 30 to render a predicted navigated pose of end-effector 40, whereby continuous positioning controller 50 (FIG. 1) may generate continuous positioning data 51 informative of a corrective positioning by interventional device 30 of end-effector 40 to a target pose based on the predicted navigated pose of end-effector 40.

Figure 4A:
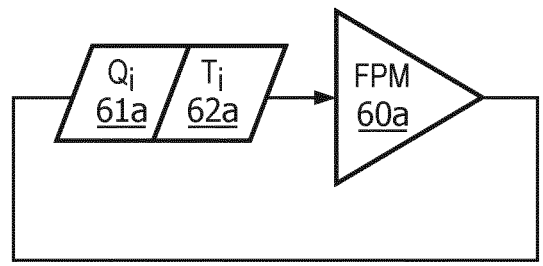
FIGS. 4A-4E illustrate first exemplary embodiments of a forward predictive model and a forward predictive method of the present disclosure.
Figure 17:
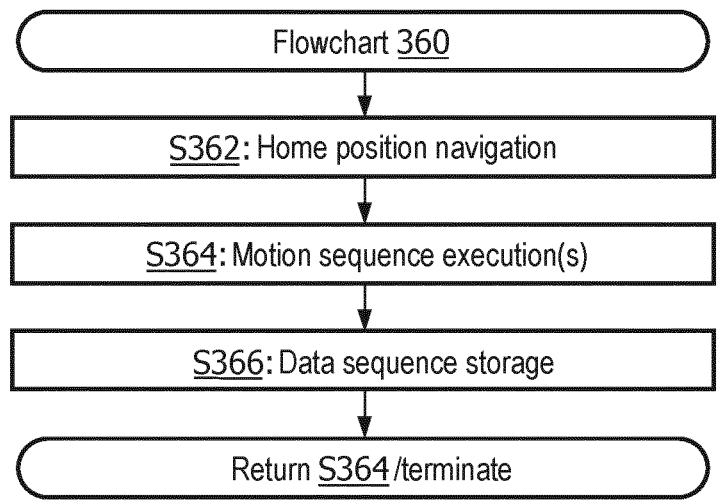
Figure 18:
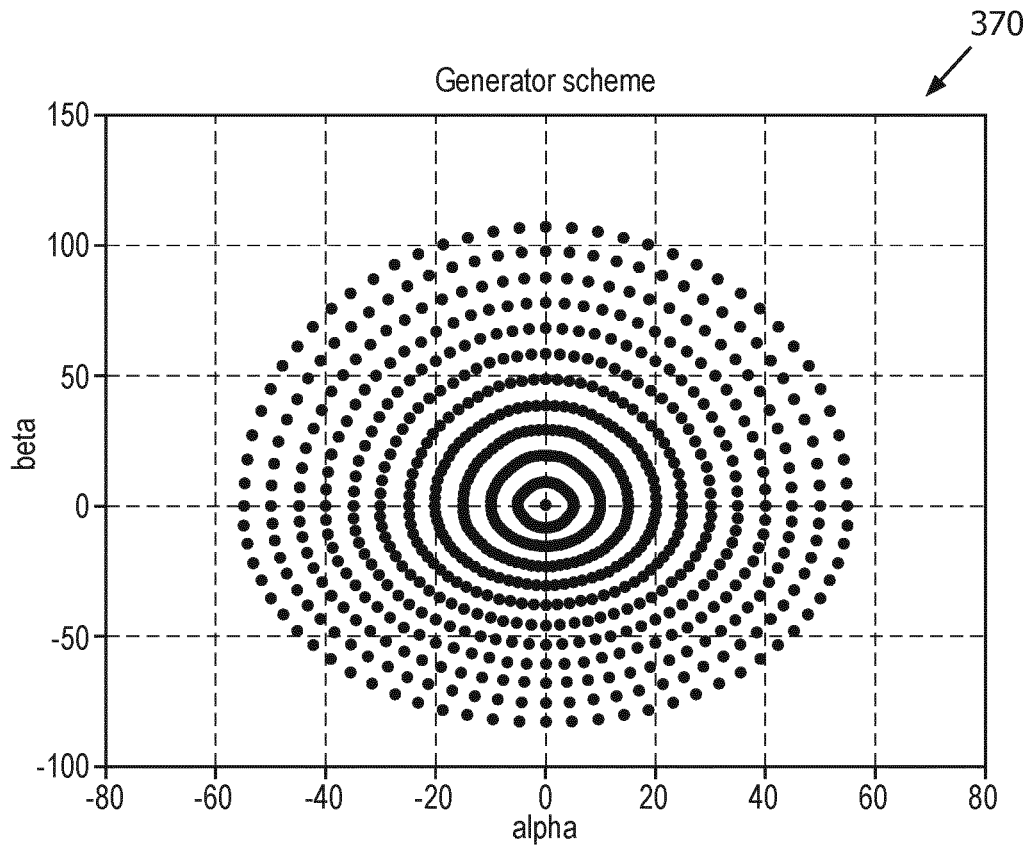

More particularly, referring to FIG. 4A, a training phase of forward predictive model 60a involves a training controller (not shown) configured to interpret ground-truth training dataset D as exemplary taught in a subsequent description of FIGS. 16-18 of the present disclosure. The dataset D consists of n sequences W that contains i data points represented by a 2-tuple: $d_i=(T_i, Q_i)$. The 2-tuple consists of an end-effector pose (T ∈ SE (3)) 62a and a sequence of j consecutive joint variables (Q ∈ ($q_t$, $q_{t+1}$ ... $q_{t+j}$)) 61a acquired at sequential time points starting from t to t+j. Entry $q_t$ stands for all joint variables that are controlled by the robot controller (not shown).

In practice, training dataset D is a collection of expert data with reasonable coverage of different navigations of interventional device 30. To this end, the diverse dataset training dataset D for learning should incorporate manufacturing differences between various types of robots, performance characteristics, wear and tear of the hardware components, and other system dependent and independent factors, such as temperature or humidity of the environment in which robot operates.

Figure 4B:
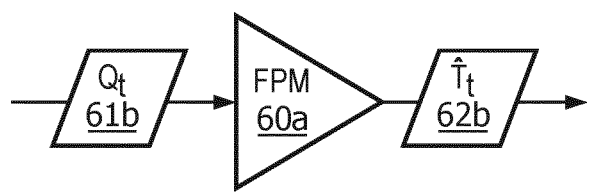

Referring to FIG. 4B, an application phase of forward predictive model 60a involves continuous positioning controller 50 executing a deep learning type algorithm using feed-forward predictive model 60a for regression of the commanded position motion of interventional device 30 to a navigated pose of end-effector 40. Forward predictive model 60a is configured to infer the pose ($\hat{T}$ ∈ SE(3)) 62b of end-effector 40 given a sequence Q of j consecutive joint variables 61b of interventional device 30 (e.g., parameters α, β as shown in FIG. 3B).

Figure 4C:
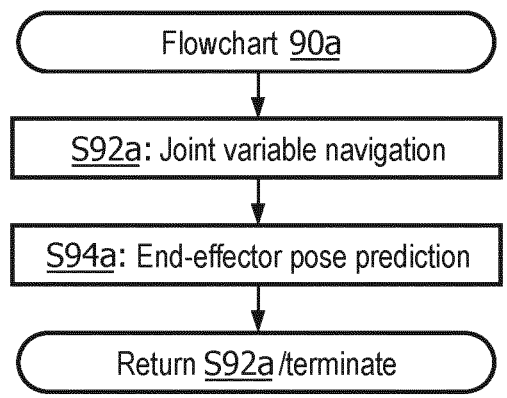
Figure 4D:
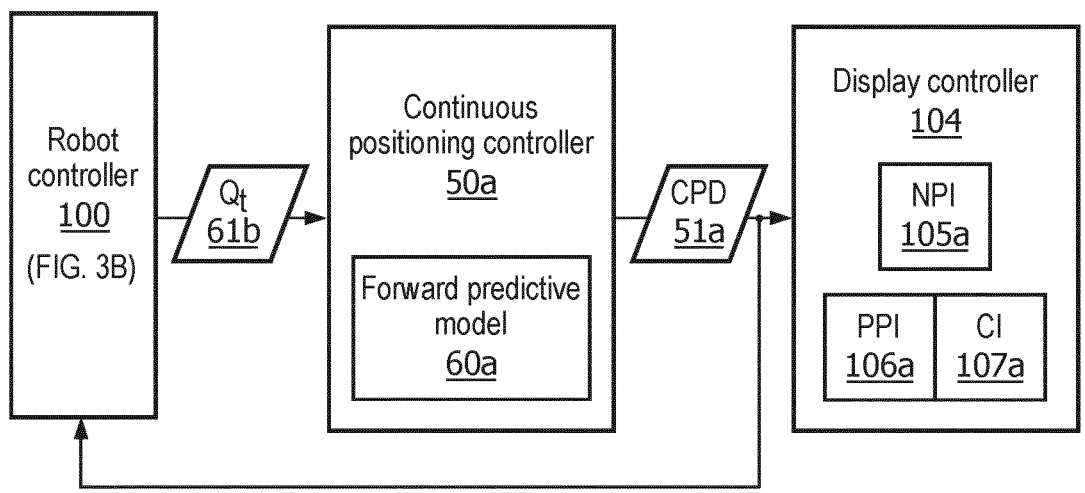
Figure 4E:
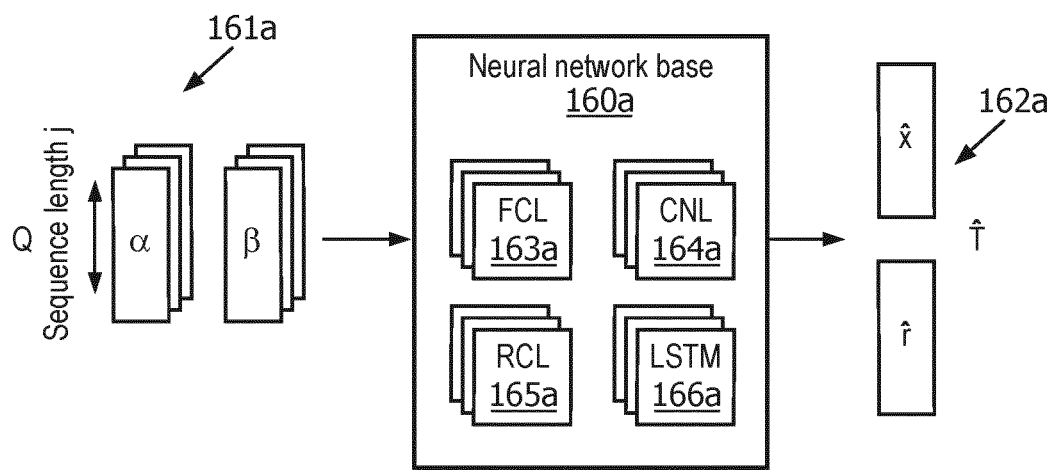

In one embodiment as shown in FIG. 4E, forward predictive model 60a employs a neural network base 160a including an input layer, hidden layers and an output layer derived from a combination of one or more fully connected layers (FCL) 163a, one or more convolutional layers (CNL) 164a, one or more recurrent layers (RCL) 165a, and one or more long term short memory (LSTM) layers 166a.

In practice, the combination of layers is configured to implement a regression of joint variables Q to pose 7.

In one embodiment for implementing a regression of joint variables Q to pose $\hat{T}$, neural network base 160a includes a set of N number of fully connected layers 163a.

In a second embodiment for implementing a regression of joint variables Q to pose $\hat{T}$, neural network base 160a includes a set of N convolutional layers 164a followed by either a set of M fully connected layers 163a or a set of W recurrent layers 165a or a set of W long term short memory layers 166a.

In a third embodiment for implementing a regression of joint variables Q to pose $\hat{T}$, neural network base 160a includes a set of N convolutional layers 164a followed combination of a set of M fully connected layers 163a and a set of W recurrent layers 165a or a set W of long term short memory layers 166a.

In practice, a fully connected layer 163a may include K neurons, where N, M, W, K may be any positive integer, and values may vary depending on the embodiments. For example, N may be about 8, M may be about 2, W may be about 2, and K can be about 1000. Alson, a convolutional layer 164a may implement a non-linear transformation, which may be a composite function of operations (e.g., batch normalization, rectified linear units (ReLU), pooling, dropout and/or convolution), and a convolutional layer 164a may also include a non-linearity function (e.g. including rectified non-linear ReLU operations) configured to extract rectified feature maps.

Further in practice, one of the layers 163a or 164a serve as an input layer for inputting a sequence 161a of joint variables Q, whereby a size of the sequence of joint variables Q may be≥1, and one of the layers 163a, 165a and 166a may serve as an output layer for outputting a pose 162a of end-effector 40 in Cartesian space (e.g., a translation and a rotation of the end-effector 40 in Cartesian space). The outputted pose of end-effector 40 in Cartesian space may be represented as vectorial parametrization and/or non-vectorial parametrization of a rigid-body position and orientation. More particularly, the parametrizations may be in the form of Euler angles, quaternions, matrix, exponential map, and/or angle-axis representing rotations and/or translations (e.g., including a direction and a magnitude for the translations).

Also in practice, the output layer may be a non-linear fully connected layer 163a that gradually shrinks a high-dimensional output of the last convolutional layer 164a of neural network base 160a to produce a set of output variables.

In training, training weights of forward predictive model 60a are constantly updated by comparing the outputs inferred forward predictive model ($\hat{T}$)—given input sequence Q—with ground-truth end-effector pose $T_i$ from a batch of training datasets D, which may be systematically or randomly selected from data memory (not shown). More particularly, the coefficients for the filters may be initialized with predefined or arbitrary values. The coefficients for the filters are applied to the batch of training datasets D via a forward propagation, and are adjusted via a backward propagation to minimize any output error.

In application, forward predictive model 60a infers the pose ($\hat{T}$) 62a of end-effector 40 given a sequence Q of j consecutive joint variables 62a.

Still referring to FIG. 4E, the neural architecture of the exemplary embodiment of forward predictive model 60a as illustrates has a unique number of layers, depending on the complexity of the task, which is specified in the output layer 169a defined to predict the pose ($\hat{T}$) 62a of the end-effector 40 given the sequence Q of j consecutive joint variables 61a. Loss function for training of this neural architecture may be defined as a sum of Euclidean distances between translational and rotational components, such as $$\text{loss} = \|\hat{x} - x\|_2 + \left\|\hat{r} - \frac{r}{\|r\|}\right\|_2.$$

Referring to FIG. 4C and FIG. 4D, a stage S92a of an exemplary interventional procedure 90a employing TEE probe 130 (FIG. 3A) and robot controller 100 (FIG. 3B) and encompasses robot controller 100 receiving a position of TEE probe 130 as joint variables and sending movement signals to handle 132 (FIG. 3A) of TEE probe 130. Using motorized knobs, handle 132 pull/loosen the tendons of TEE probe 130, which will result in the motion of the end-effector 140 (FIGS. 3C-3F) to a target pose. In practice, the position of TEE probe 130 as joint variables may be indicated by a user or an external tracking device or a guidance system.

A stage S94a of procedure 90a involves robot controller 100, forward predictive model 50a and a display controller 104. Robot controller 100 stores and communicates the sequence of consecutive joint variables (Q) 61a to forward predictive model 60a that predicts the navigated pose i of the end effector 140. Continuous positioning controller 50a generates a confidence ratio of the prediction derived from uncertainty multiple feedforward iterations of forward predictive model 60a performed with dropout enabled stochastically as known in the art of the present disclosure.

Forward predictive model 50a communicates continuous positioning data 51a including the predicted navigated pose $\hat{T}$ of the end effector 140 and the confidence ratio to a display controller 104, which in turn controls a display of an image 105a of the navigated pose of end-effector 140, an image 106a of the navigated pose of end-effector 140 and the confidence ratio for guidance purposes to end-effector 140 to the target pose.

FIGS. 5A-5E illustrate a training and an application of an inverse predictive model 70a of the present disclosure trained to on inverse kinematics of an interventional device 30 (FIG. 1) predictive of a positioning motion of interventional device 30 to thereby, during an interventional procedure, facilitate an application of inverse predictive model 70a to target pose (T) 71a of end-effector 40 to render a joint variable motion (q) $72_t$ of interventional device 30, whereby continuous positioning controller 50 (FIG. 1) may generate continuous positioning commands controlling a repositioning by interventional device 30 of the end-effector 40 to the target pose based on the predicted positioning motion of the interventional device 40.

Figure 5A:
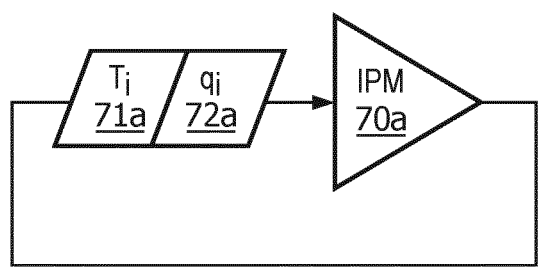
FIGS. 5A-5E illustrate first exemplary embodiments of an inverse predictive model and an inverse predictive method of the present disclosure.

More particularly, referring to FIG. 5A, a training phase of inverse predictive model 70a involves a training controller (not shown) configured to interpret ground-truth training dataset D as exemplary taught in the description of FIGS. 17-18. The dataset D consists of n sequences W that contains i data points represented by a 2-tuple: $d_i=(T_i, Q_i)$. The 2-tuple consists of an end-effector pose (T ∈ SE(3)) 71a and a sequence of j consecutive joint variables (Q ∈ ($q_t$, $q_{t+1}$ ... $q_{t+j}$)) 72a acquired at sequential time points starting from t to t+j. Entry $q_t$ stands for all joint variables that are controlled by the robot controller (not shown). Variable j may also equal to 1, meaning predictive model will be trained to infer single set of joint variables.

In practice, training dataset D is a collection of expert data with reasonable coverage of different navigations of interventional device 30. To this end, the diverse dataset training dataset D for learning should incorporate mechanical differences between various types of robots, wear and tear of the hardware components, and other system dependent factors.

Figure 5B:
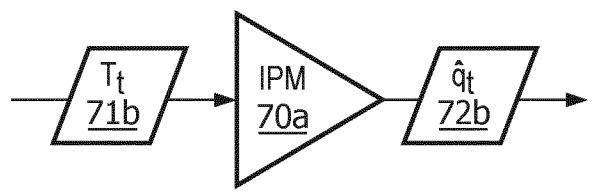

Referring to FIG. 5B, an application phase of inverse predictive model 70a involves continuous positioning controller 50 executing a deep learning type algorithm using inverse predictive model 70a for motion regression. Inverse predictive model 70a is configured to infer sequence $\hat{Q}$ off consecutive joint variables $72_t$ (e.g., parameters α, β as shown in FIG. 3B) to reach the pose (T ∈ SE(3)) 71t of end-effector 40.

Figure 5C:
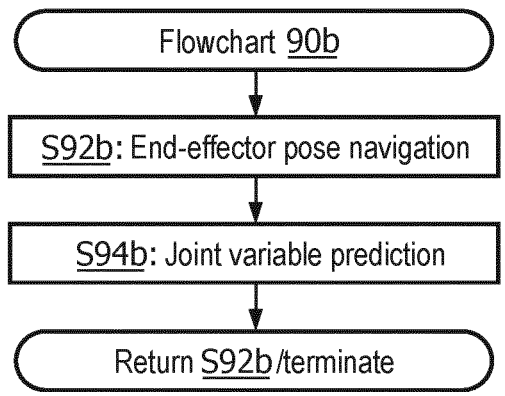
Figure 5D:
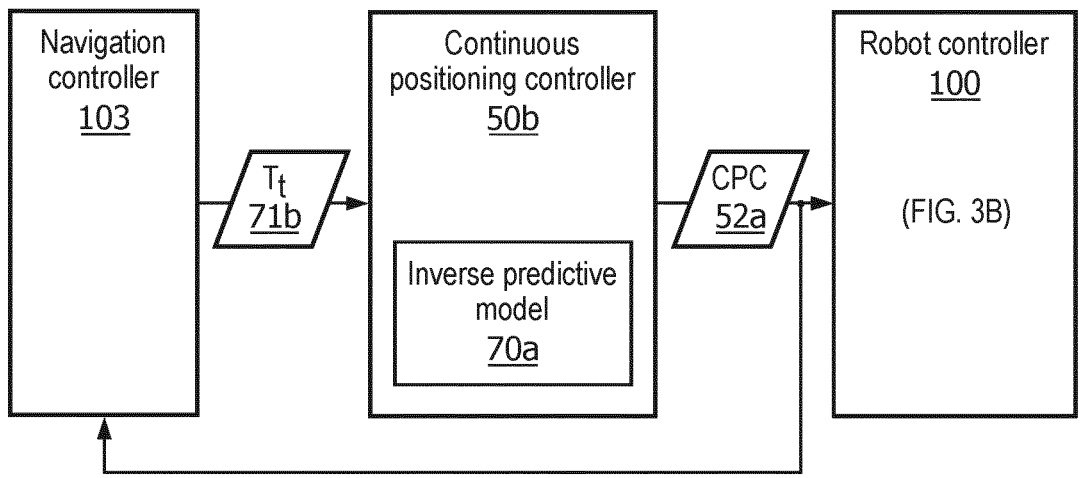
Figure 5E:
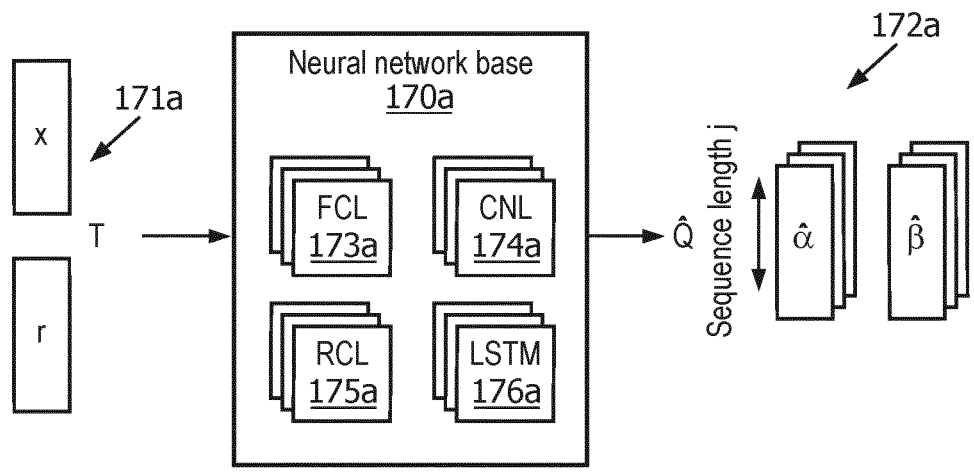

In one embodiment as shown in FIG. 5E, inverse predictive model 70a employs a neural network base 170a including an input layer, hidden layers and an output layer derived from a combination of one or more fully connected layers (FCL) 173a, one or more convolutional layers (CNL) 174a, one or more recurrent layers (RCL) 175a, and one or more long term short memory (LSTM) layers 176a.

In practice, the combination of layers is configured to implement a regression of pose T to joint variables $\hat{Q}$.

In one embodiment for implementing a regression of pose T to joint variables $\hat{Q}$, neural network base 170a includes a set of N number of fully connected layers 173a.

In a second embodiment for implementing a regression of pose T to joint variables $\hat{Q}$, neural network base 170a includes a set of N convolutional layers 174*a* followed by either a set of M fully connected layers 173*a* or a set of W recurrent layers 175*a* or a set of W long term short memory layers 176*a*.

In a third embodiment for implementing a regression of pose T to joint variables $\hat{Q}$, neural network base 170*a* includes a set of N convolutional layers 174*a* followed combination of a set of M fully connected layers 173*a* and a set of W recurrent layers 175*a* or a set W of long term short memory layers 176*a*.

In practice, a fully connected layer 173*a* may include K neurons, where N, M, W, K may be any positive integer, and values may vary depending on the embodiments. For example, N may be about 8, M may be about 2, W may be about 2, and K can be about 1000. Also, a convolutional layer 174*a* may implement a non-linear transformation, which may be a composite function of operations (e.g., batch normalization, rectified linear units (ReLU), pooling, drop-out and/or convolution), and a convolutional layer 174*a* may also include a non-linearity function (e.g. including rectified non-linear ReLU operations) configured to extract rectified feature maps.

Further in practice, one of the layers 173*a* or 174*a* serve as an input layer for inputting pose 171*a* of end-effector 40 in Cartesian space (e.g., a translation and a rotation of the end-effector 40 in Cartesian space), and one of the layers 173*a*, 175*a* and 176*a* may serve as an output layer for outputting a sequence 172*a* of joint variables Q, whereby a size of the sequence of joint variables Q may be≥1. The inputted pose of end-effector 40 in Cartesian space may be represented as vectorial parametrization and/or non-vectorial parametrization of a rigid-body position and orientation. More particularly, the parametrizations may be in the form of Euler angles, quaternions, matrix, exponential map, and/or angle-axis representing rotations and/or translations (e.g., including a direction and a magnitude for the translations).

Also in practice, the output layer may be a non-linear fully connected layer 173*a* that gradually shrinks a high-dimensional output of the last convolutional layer 174*a* of neural network base 170*a* to produce a set of output variables.

In training, training weights of inverse predictive model 70*a* are constantly updated by comparing the output from the inverse predicted model Q—given as input a ground-truth end effector pose T—with a ground-truth sequence $Q_t$ from a batch of training datasets D, which may be systematically or randomly selected from data memory (not shown). More particularly, the coefficients for the filters may be initialized with predefined or arbitrary values. The coefficients for the filters are applied to the batch of training datasets D via a forward propagation, and are adjusted via a backward propagation to minimize any output error.

In application, inverse predictive model 70*a* infers sequence $\hat{Q}$ off consecutive joint variables 72*b*(e.g., parameters α, β as shown in FIG. 3B) to reach the provided pose (T ∈ SE(3)) 71*b* of end-effector 40.

Still referring to FIG. 5E, the neural architecture of the exemplary embodiment of inverse predictive model 70*a* as illustrates has a unique number of layers, depending on the complexity of the task, which is specified in the output layer 179*a* defined to predict sequence Q of j consecutive joint variables 72*b* (e.g., parameters α, β as shown in FIG. 3B) to reach the pose (T ∈ SE(3)) 71*b* of end-effector 40. A mean squared error (MSE) may be used as a loss function.

Referring to FIG. 5C and FIG. 5D, a stage S92*b* of an exemplary interventional procedure 90*b* employing TEE probe 130 (FIG. 3A) and a navigation controller 103 and encompasses navigation controller 103 determining the target pose of end-effector 140 and sending the target pose 71*a* to inverse predictive model 70*a*. In practice, navigation controller 130 may implement any known guidance algorithm known in the art of the present disclosure.

A stage S94A of procedure 90*b* involves inverse predictive model 70*a* and robot controller 100. Inverse predictive model 70*a* infers sequence $\hat{Q}$ of j consecutive joint variables 72*a* (e.g., parameters α, β as shown in FIG. 3B) to reach the pose (T ∈ SE(3)) 71*a* of end-effector 40, and continuous positioning controller 50*b* communicates a command controller 104 to control a positioning of end-effector 50 via the interventional device 30 of end-effector 40 to the target pose based on the predicted positioning motion of the interventional device 40.

FIGS. 6A-6E illustrate a training and an application of a forward predictive model 60*b* of the present disclosure trained on forward kinematics of an interventional device 30 (FIG. 1) predictive of a navigated pose of an end-effector 40 (FIG. 1) to thereby, during an interventional procedure, facilitate an application of forward predictive model 60*b* to a commanded n-vector of joint velocities of interventional device 30 to render a predicted linear velocity and/or angular velocity of end-effector 40, whereby continuous positioning controller 50 (FIG. 1) may generate continuous positioning data 51 informative of a repositioning by interventional device 30 of end-effector 40 to a target pose based on the predicted linear velocity and/or angular velocity of end-effector 40.

Figure 6A:
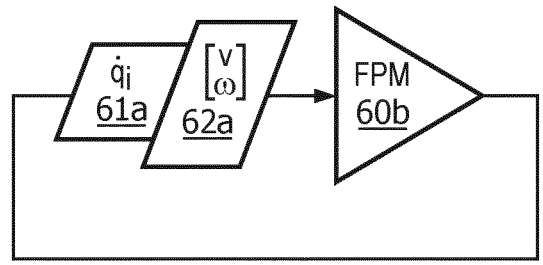
FIGS. 6A-6E illustrate second exemplary embodiments of a forward predictive model and a forward predictive method of the present disclosure.

More particularly, referring to FIG. 6A, a training phase of forward predictive model 60*b* involves a training controller (not shown) configured to interpret ground-truth training dataset D as exemplary taught in the description of FIGS. 16-18. The dataset D consists of n sequences W that contains i data points represented by a 2-tuple:

$$d_i = \left( \dot{Q}_i, \begin{bmatrix} v_i \\ \omega_i \end{bmatrix} \right).$$

The 2-tuple consists of commanded sequence of j consecutive joint velocities ($\dot{Q} \in (\dot{q}_t, \dot{q}_{t+1} \ldots \dot{q}_{t+j})$) 61*b* and linear velocity and/or angular velocity 62*b* of the end effector $$\begin{bmatrix} v \\ \omega \end{bmatrix}.$$

Entry $\dot{q}_i$ stands for all joint velocities that are controlled by the robot controller (not shown). Sequence may also contain only one entry.

In practice, training dataset D is a collection of expert data with reasonable coverage of different navigations of interventional device 30. To this end, the diverse dataset training dataset D for learning should incorporate mechanical differences between various types of robots, wear and tear of the hardware components, and other system dependent factors.

Figure 6B:
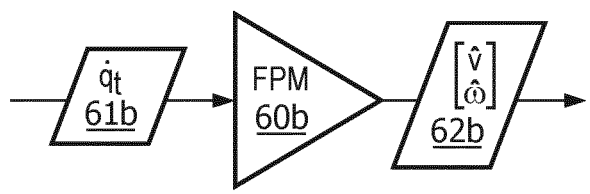

Referring to FIG. 6B, an application phase of forward predictive model 60*b* involves continuous positioning controller 50 executing a deep learning type algorithm using feed-forward predictive model 60*b* for end effect motion regression. Forward predictive model 60*b* is configured to infer the linear velocity and/or angular velocity 62*b* of end-effector 40 given n-vector of joint velocities 61*b* of interventional device 30.

Figure 6C:
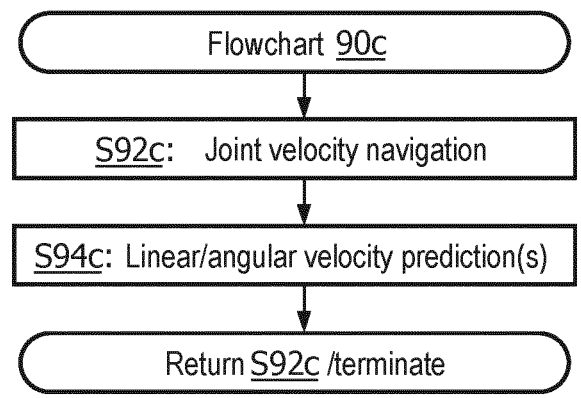
Figure 6D:
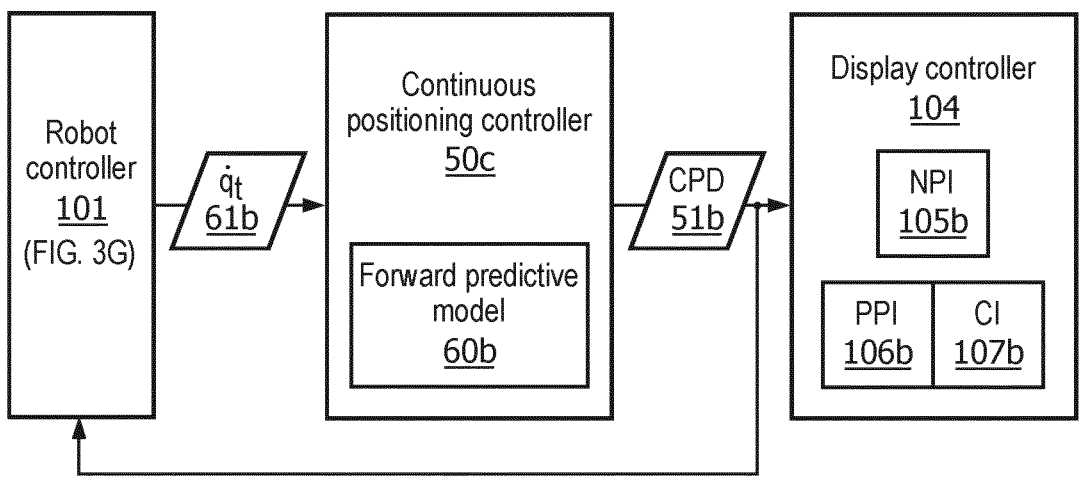
Figure 6E:
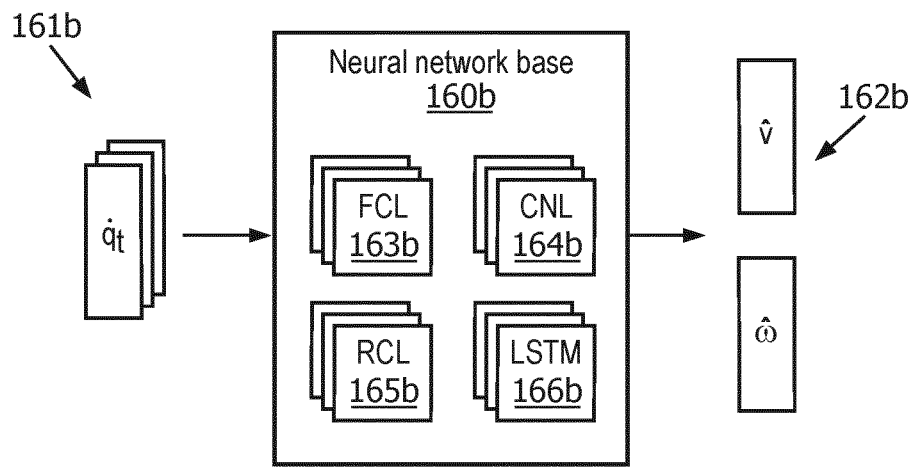

In one embodiment as shown in FIG. 6E, forward predictive model 60b employs a neural network base 160b including an input layer, hidden layers and an output layer derived from a combination of one or more fully connected layers (FCL) 163b, one or more convolutional layers (CNL) 164b, one or more recurrent layers (RCL) 165b, and one or more long term short memory (LSTM) layers 166b.

In practice, the combination of layers is configured to implement a regression of joint velocities of the interventional device 30 to a linear velocity and/or an angular velocity of end-effector 40.

In one embodiment for implementing a regression of joint velocities of the interventional device 30 to a linear velocity and/or an angular velocity of end-effector 40, neural network base 160b includes a set of N number of fully connected layers 163b.

In a second embodiment for implementing a regression of joint velocities of the interventional device 30 to a linear velocity and/or an angular velocity of end-effector 40, neural network base 160b includes a set of N convolutional layers 164b followed by either a set of M fully connected layers 163b or a set of W recurrent layers 165b or a set of W long term short memory layers 166b.

In a third embodiment for implementing a regression of joint velocities of the interventional device 30 to a linear velocity and/or an angular velocity of end-effector 40, neural network base 160b includes a set of N convolutional layers 164b followed combination of a set of M fully connected layers 163b and a set of W recurrent layers 165b or a set W of long term short memory layers 166b.

In practice, a fully connected layer 163b may include K neurons, where N, M, W, K may be any positive integer, and values may vary depending on the embodiments. For example, N may be about 8, M may be about 2, W may be about 2, and K can be about 1000. Also, a convolutional layer 164b may implement a non-linear transformation, which may be a composite function of operations (e.g., batch normalization, rectified linear units (ReLU), pooling, dropout and/or convolution), and a convolutional layer 164b may also include a non-linearity function (e.g. including rectified non-linear ReLU operations) configured to extract rectified feature maps.

Further in practice, one of the layers 163b or 164b serve as an input layer for inputting a sequence of j consecutive joint velocities ($\dot{Q} \in (\dot{q}_t, \dot{q}_{t+1} \ldots \dot{q}_{t+j})$), whereby a size of the a sequence of j consecutive joint velocities ($\dot{Q} \in (\dot{q}_t, \dot{q}_{t+1} \ldots \dot{q}_{t+j})$) may be ≥1, and one of the layers 163b, 165b and 166b may serve as an output layer for outputting a linear and angular velocity of the end effector $$\begin{bmatrix} \hat{v} \\ \hat{\omega} \end{bmatrix}$$

as regressed from last fully-connected layer (e.g. 6 units, 3 units for linear and 3 units for angular velocity) with linear or non-linear activation function.

In training, training weights of forward predictive model 60b are constantly updated by comparing the predicted linear and angular velocity $$\begin{bmatrix} \hat{v} \\ \hat{\omega} \end{bmatrix}$$

via forward velocity predictive model the—given a sequence of joint velocities—with linear velocity and/or angular velocity 62b from a batch of training datasets D, which may be systematically or randomly selected from data memory (not shown). More particularly, the coefficients for the filters may be initialized with predefined or arbitrary values. The coefficients for the filters are applied to the batch of training datasets D via a forward propagation, and are adjusted via a backward propagation to minimize any output error.

In application, forward predictive model 60b infer the linear velocity and/or angular velocity 62b of end-effector 40 given sequence of joint velocities 61b of interventional device 30.

Still referring to FIG. 6E, the neural architecture consisting of inputs, neural network base described previously, and outputs. Input is a sequence of joint velocities, and output is linear and angular velocity that could be regressed from fully-connected layer with 6 units. The loss function may be a MSE as listed:

$$MSE = \frac{1}{n}\sum_{i=1}^{n}\left(\begin{bmatrix} v \\ \omega \end{bmatrix} - \begin{bmatrix} \hat{v} \\ \hat{\omega} \end{bmatrix}\right).$$

Referring to FIG. 6C and FIG. 6D, a stage S92c of an exemplary interventional procedure 90c employing robot 230 (FIG. 3A), TTE probe 240 (FIG. 3A), and robot controller 101 (FIG. 3G) and encompasses robot controller 101 receiving a position of TTE probe 240 as n-vector of joint velocities 61b of interventional device 30 and sending n-vector of joint velocities 61b of interventional device 30 to robot 230. In practice, the position of TTE probe 240 as n-vector of joint velocities 61b of interventional device 30 may be indicated by a user or an external tracking device or a guidance system.

A stage S94c of procedure 90c involves robot controller 101, forward predictive model 50a and a display controller 104. Robot controller 101 stores and communicates the n-vector of joint velocities 61b of interventional device 30 to forward predictive model 60b that predicts the linear velocity and/or angular velocity 62b of TTE probe 240. Continuous positioning controller 50c generates a confidence ratio of the prediction derived from uncertainty multiple feedforward iterations of forward predictive model 60b performed with dropout enabled stochastically as known in the art of the present disclosure. Forward predictive model 60b communicates continuous positioning data 51b including a predicted navigated pose P of the TTE probe 240 derived from the predicted linear velocity and/or angular velocity 62b of TTE probe 240, and further including the confidence ratio to a display controller 104, which in turn controls a display of an image 105a of the navigated pose of TTE probe 240, an image 106a of the navigated pose TTE probe 240 and the confidence ratio for guidance purposes to end-effector 240 to the target pose.

FIGS. 7A-7E illustrate a training and an application of an inverse predictive model 70b of the present disclosure trained to on inverse kinematics of an interventional device 30 (FIG. 1) predictive of a positioning motion of interventional device 30 to thereby, during an interventional procedure, facilitate an application of inverse predictive model 70b to a target pose of end-effector 40 to render a predicted positioning motion of interventional device 30, whereby continuous positioning controller 50 (FIG. 1) may generate continuous positioning commands controlling a repositioning by interventional device 30 of the end-effector 40 to the target pose based on the predicted positioning motion of the interventional device 40.

Figure 7A:
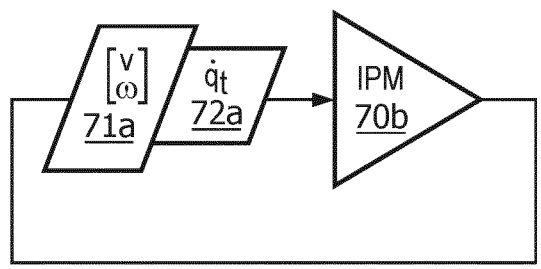
FIGS. 7A-7E illustrate second exemplary embodiments of an inverse predictive model and an inverse predictive method of the present disclosure.

More particularly, referring to FIG. 7A, a training phase of inverse predictive model 70b involves a training controller (not shown) configured to interpret ground-truth training dataset D as exemplary taught in the description of FIGS. 17-18. The dataset D consists of n sequences W that contains i data points represented by a 2-tuple:

$$d_i = \left( \begin{bmatrix} v_i \\ \omega_i \end{bmatrix}, \dot{Q}_i \right).$$

The 2-tuple consists of a linear velocity and/or angular velocity of the end effector and sequence of consecutive joint velocities ($\dot{q}_t$) acquired at sequential time points starting from t to t+j. Entry $q_t$ stands for all joint velocities that are controlled by the robot controller (not shown).

In practice, training dataset D is a collection of expert data with reasonable coverage of different navigations of interventional device 30. To this end, the diverse dataset training dataset D for learning should incorporate mechanical differences between various types of robots, wear and tear of the hardware components, and other system dependent factors.

Figure 7B:
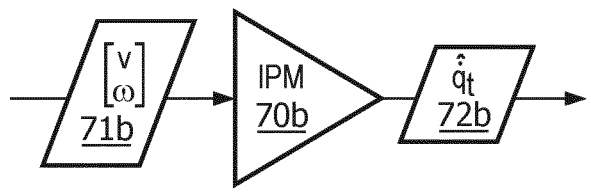

Referring to FIG. 7B, an application phase of inverse predictive model 70b involves continuous positioning controller 50 executing a deep learning type algorithm using inverse predictive model 70b for joint velocity regression. Inverse predictive model 70b is configured to infer a n-vector of joint velocities 61b of interventional device 30 given a linear velocity and/or angular velocity 62b of end-effector 40.

Figure 7C:
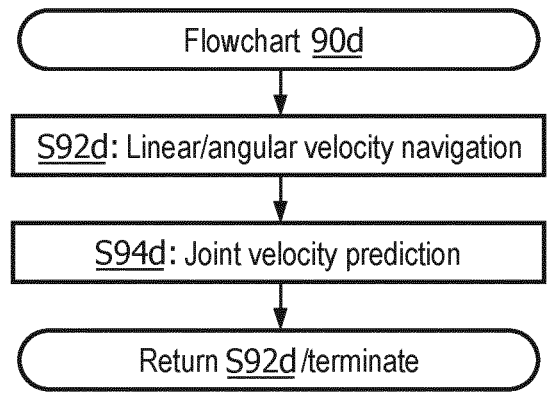
Figure 7D:
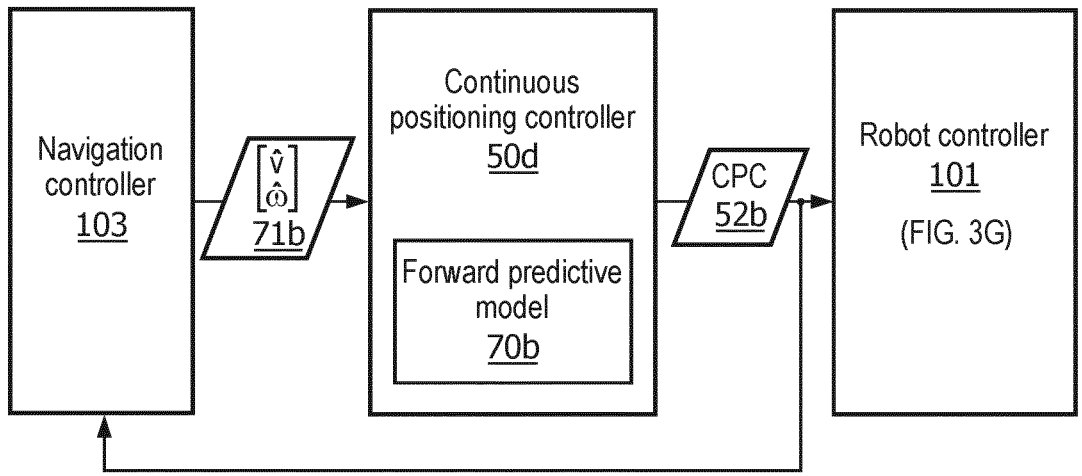
Figure 7E:
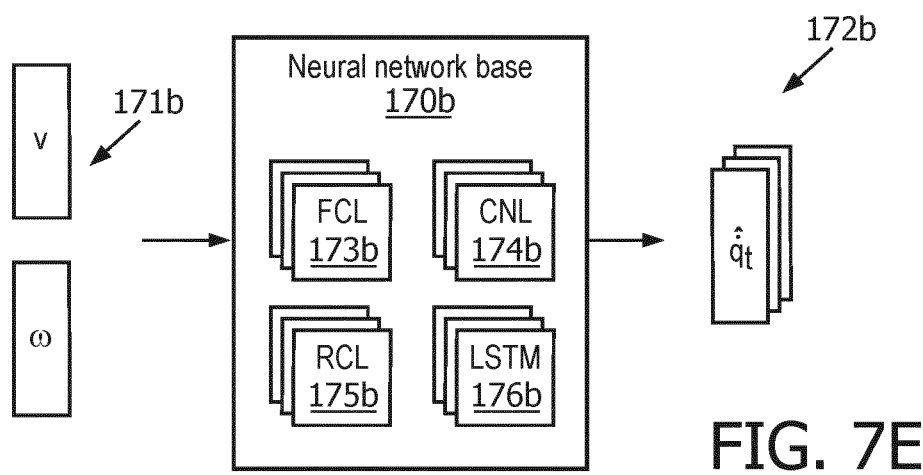

In one embodiment as shown in FIG. 7E, inverse predictive model 70b employs a neural network base 170b including an input layer, hidden layers and an output layer derived from a combination of one or more fully connected layers (FCL) 173b, one or more convolutional layers (CNL) 174b, one or more recurrent layers (RCL) 175b, and one or more long term short memory (LSTM) layers 176b.

In practice, the combination of layers is configured to implement a regression of a linear velocity and/or an angular velocity of end-effector 40 to joint velocities of the interventional device 30.

In one embodiment for implementing a regression of a linear velocity and/or an angular velocity of end-effector 40 to joint velocities of the interventional device 30, neural network base 170b includes a set of N number of fully connected layers 173b.

In a second embodiment for implementing a regression of a linear velocity and/or an angular velocity of end-effector 40 to joint velocities of the interventional device 30, neural network base 170b includes a set of N convolutional layers 174b followed by either a set of M fully connected layers 173b or a set of W recurrent layers 175b or a set of W long term short memory layers 176b.

In a third embodiment for implementing a regression of a linear velocity and/or an angular velocity of end-effector 40 to joint velocities of the interventional device 30, neural network base 170b includes a set of N convolutional layers 174b followed combination of a set of M fully connected layers 173b and a set of W recurrent layers 175b or a set W of long term short memory layers 176b.

In practice, a fully connected layer 173b may include K neurons, where N, M, W, K may be any positive integer, and values may vary depending on the embodiments. For example, N may be about 8, M may be about 2, W may be about 2, and K can be about 1000. Also, a convolutional layer 174b may implement a non-linear transformation, which may be a composite function of operations (e.g., batch normalization, rectified linear units (ReLU), pooling, dropout and/or convolution), and a convolutional layer 174b may also include a non-linearity function (e.g. including rectified non-linear ReLU operations) configured to extract rectified feature maps.

Further in practice, one of the layers 173b or 174b serve as an input layer for inputting angular and linear velocity $$\begin{bmatrix} v \\ \omega \end{bmatrix},$$

and one of the layers 173b, 175b and 176b may serve as an output layer for outputting a a sequence of j consecutive joint velocities ($Q \in (\dot{q}_t, \dot{q}_{t+1} \ldots \dot{q}_{t+j})$) that provided as output from LSTM layers 176b. Alternatively, single joint velocities may be regressed from fully-connected layer 173b consisting of m units, each unit for every join in the robot controlled by the robot controller. Fully-connected layer 173b may have linear or non-linear activation functions.

In training, training weights of inverse predictive model 70b are constantly updated by comparing the predicted sequence of joint velocities $\dot{Q}$—given a linear and angular velocity at input $$\begin{pmatrix} v_i \\ \omega_i \end{pmatrix} -$$

with the ground-truth sequence $\hat{Q}_i$ of joint velocities from a batch of training datasets D, which may be systematically or randomly selected from data memory (not shown). More particularly, the coefficients for the filters may be initialized with predefined or arbitrary values. The coefficients for the filters are applied to the batch of training datasets D via a forward propagation, and are adjusted via a backward propagation to minimize any output error.

In application, inverse predictive model 70b infers a n-vector of joint velocities 61b of interventional device 30 given a linear velocity and/or angular velocity 62b of end-effector 40.

Still referring to FIG. 7E, the neural architecture of the exemplary embodiment of inverse velocity model consisting of inputs, neural network base, and outputs. Input is angular and linear velocity $$\begin{bmatrix} v \\ \omega \end{bmatrix}$$

and output is a sequence $\hat{Q}$ of joint velocities that provided as output from LSTM layers. Alternatively, single joint velocities may be regressed from fully-connected layer consisting of m units, each unit for every join in the robot controlled by the robot controller. Fully-connected layer may have linear or non-linear activation functions.

Referring to FIG. 7C and FIG. 7D, a stage S92d of an exemplary interventional procedure 90d employing TTE probe 240 (FIG. 3G) and a navigation controller 103 and encompasses navigation controller 103 determining a linear velocity and/or angular velocity 62*b* of TTE probe 240 to a target pose and sending the linear velocity and/or angular velocity 62*b* to inverse predictive model 70*b*. In practice, navigation controller 130 may implement any known guidance algorithm known in the art of the present disclosure.

A stage S94*d* of procedure 90*d* involves inverse predictive model 70*b* and robot controller 101. Inverse predictive model 70*b* infers a n-vector of joint velocities 61*b* of interventional device 30 given linear velocity and/or angular velocity 62*b*, and continuous positioning controller 50*c* communicates a continuous positioning command 52*b* to robot controller 101 to thereby control a positioning of TTE probe 240 via the robot 230 (FIG. 3G) to the target pose based on the predicted positioning motion of the interventional device 40.

In practice, forward predictive model 60*a* (FIG. 4A), inverse predictive model 70*a* (FIG. 5A), forward predictive model 60*b* (FIG. 64A) and inverse predictive model 70*b* (FIG. 7A) may use additional auxiliary information, such as, for example, an image of the anatomy (e.g., ultrasound, endoscopic, or X-ray image), a force measured at the end effector and a shape of the robot. Other inputs, including information from spectral tissue sensing device, ECG or EEG signal, tissue conductivity, or other physiological signals could also be included depending on the application. For example, if the continuum-like robot operates inside the human heart, features available in the ultrasound image as well as electrophysiological signal could improve the localization of the end effector in respect to the anatomy, hence improve the guidance accuracy.

Figure 8A:
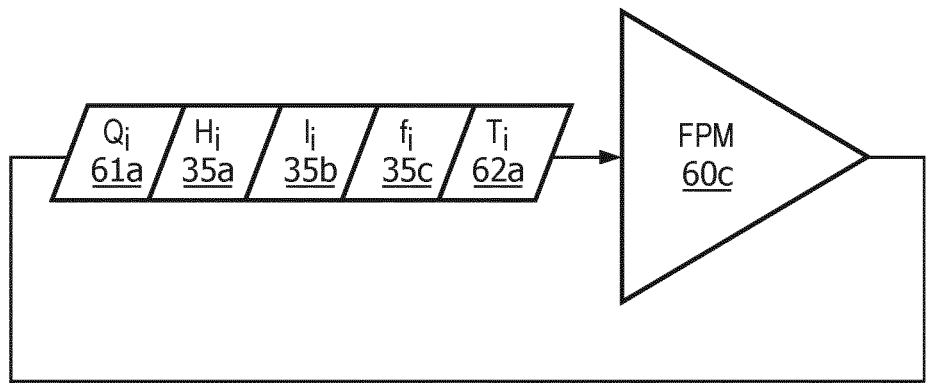
FIGS. 8A-8B illustrate third exemplary embodiments of a forward predictive model and a forward predictive method of the present disclosure.
Figure 8B:
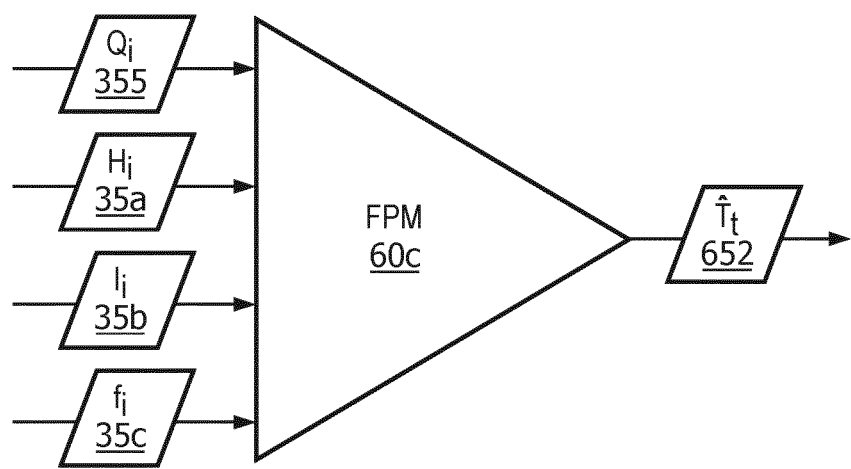

Referring to FIGS. 8A and 8B, a forward predictive model 60*c* is shown as being trained on a shape 35*a*, an image 35*b* and a force 35*c* of the interventional device in addition to forward kinematics of the interventional device in addition to sequence Q of joint variables 61*a* and end-effector poses T 62*a*. Thus, in application, forward predictive model 60*c* will be capable of predicting a navigated pose of the end-effector from sequence Q of joint variables 61*a* as well as the shape 35*a*, the image 35*b* and the force 35*c* of the interventional device.

Those having ordinary skill in the art will know how to apply shape 35*a*, an image 35*b* and a force 35*c* of the interventional device as well as any other additional auxiliary information to inverse predictive model 70*a*, forward predictive model 60*b* and inverse predictive model 70*b*. FIGS. 9A-9E illustrate a training and an application of a forward predictive model 60*d* of the present disclosure trained on the forward kinematics of interventional device 30 (FIG. 1) predictive of a navigated pose of an end-effector 40 (FIG. 1) as well as shape of the robot to thereby, during an interventional procedure, facilitate an application of forward predictive model 60*d* to sequence of consecutive shapes of an interventional device 30 with embedded OSS technology to render a predicted navigated pose of end-effector 40 as well as shape, whereby continuous positioning controller 50 (FIG. 1) may generate continuous positioning data 51*c* informative of a repositioning by interventional device 30 of end-effector 40 to a target pose based on the predicted navigated pose of end-effector 40.

Figure 9A:
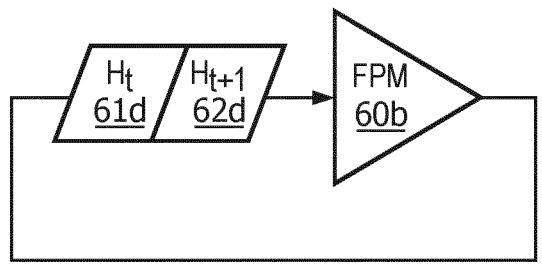
FIGS. 9A-9F illustrate fourth exemplary embodiments of a forward predictive model and a forward predictive method of the present disclosure.

More particularly, referring to FIG. 9A, a training phase a training controller (not shown) configured to interpret ground-truth training dataset D as exemplary taught in the description of FIGS. 16-18. This dataset consists of n sequences W that contains i data points represented by a 2-tuple: $d_i = (H_i, H_{i+1})$. This 2-tuple consists of a sequence of k consecutive shapes 61*d* ($H_i \in (h_t, h_{t+1} \ldots h_{t+k})$), where h $\in (p_1 \ldots p_m)$ is a set of m vectors $p_m$ that describe both the position of an OSS sensor embedded in interventional device 30 (e.g., shape-sensed guidewire) in 3D Euclidean space and auxiliary shape parameters such as strain, curvature, and twist. This 2-tuple further consists a sequence of k consecutive shapes 62*b* containing a future time point $h_{t+k+1}$ such as $H_{i+1} \in (h_{t+1}, h_{t+2} \ldots h_{t+k+1})$, where h $\in (p_1 \ldots P_m)$ is a set of m vectors $P_m$ that describe both the position of OSS interventional device 30 in 3D Euclidean space and auxiliary shape parameters such as strain, curvature, and twist.

In practice, training dataset D is a collection of expert data with reasonable coverage of different navigations of OSS interventional device 30. To this end, the diverse dataset training dataset D for learning should incorporate anatomies with different curvatures, magnitude of motion, mechanical differences between various types of robots, wear and tear of the hardware components, and other system independent factors such as temperature and humidity of the environment.

Figure 9B:
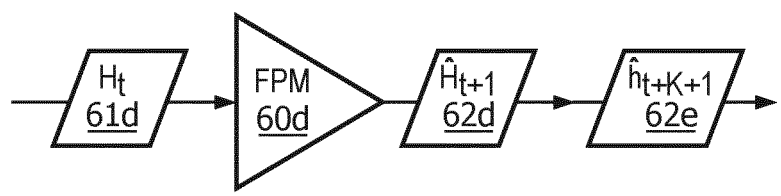

Referring to FIG. 9B, an application phase of forward predictive model 60*d* involves a continuous positioning controller 50*d* executing a deep learning type algorithm using forward with recurrent layers trained on expert data with reasonable coverage of different cases. Diverse dataset for learning incorporates various working conditions (temperature, fiber bending, etc.), different operational motion of the device, and differences in hardware (fiber, interrogator, etc.)..

Figure 9C:
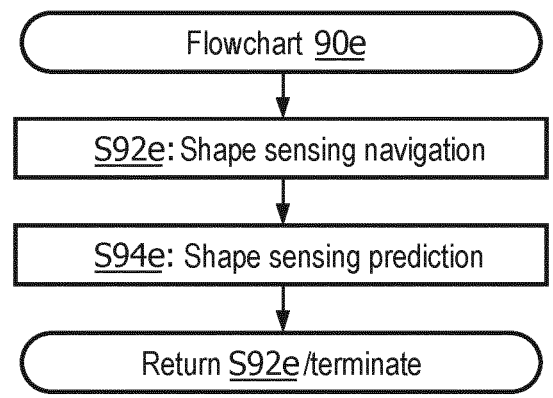
Figure 9D:
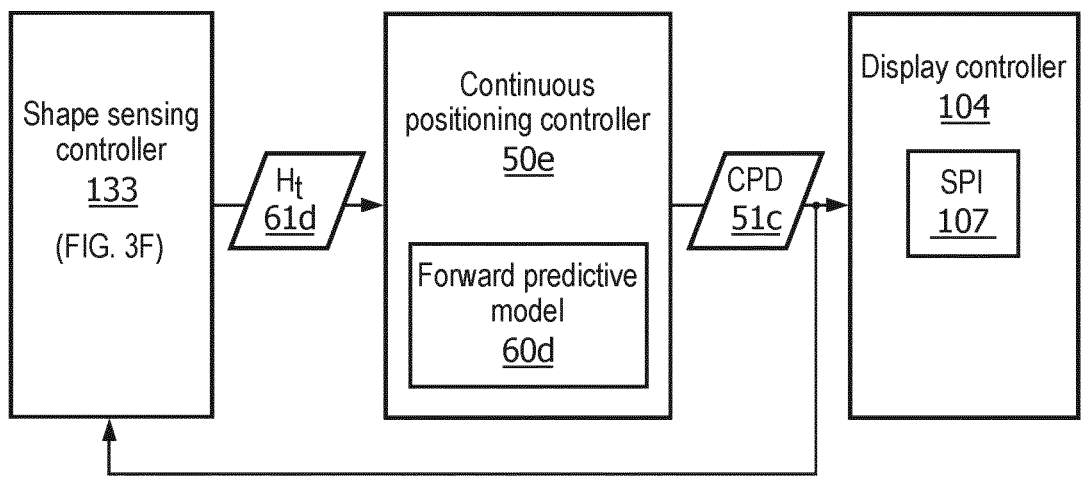
Figure 9E:
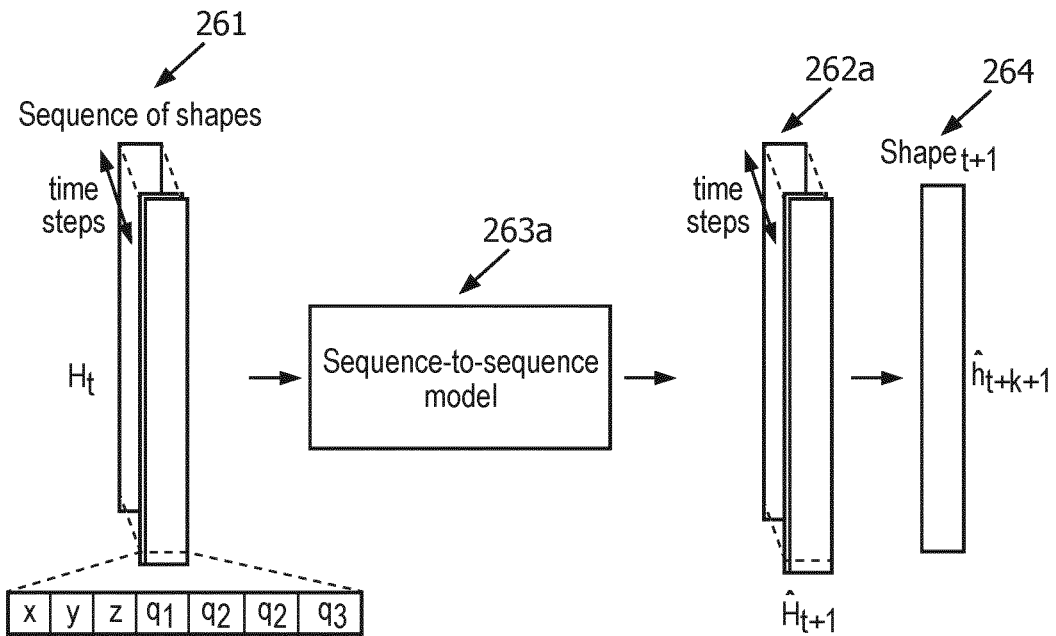

In one embodiment as shown in FIG. 9E, forward predictive model 60*d* employs a neural architecture sequentially including an input layer 163*a*, a sequence-to-sequence model 263*a*, output layer 262*a* and an extraction layer 264. The neural architecture is a deep convolutional neural network with recurrent layers that are configured to infer the future sequence $\hat{H}_{i+1}$ consisting of k shapes and therefore use the last shape $\hat{h}_{t+k+1}$ in the predicted sequence to estimate the position of OSS interventional device 30 in the future time point.

In training, training weights of forward predictive model 60*d* are constantly updated by comparing the sequence of future shapes $\hat{H}_{i+1}$—predicted by a the model given an input sequence $H_i$—with ground-truth future sequence $H_{i+1}$ from the training dataset D, which may be systematically or randomly selected from data memory (not shown). More particularly, the coefficients for the filters may be initialized with predefined or arbitrary values. The coefficients for the filters are applied to the batch of training datasets D via a forward propagation, and are adjusted via a backward propagation to minimize any output error.

In application, forward predictive model 60*d* infers the future sequence $\hat{H}_{i+1}$ consisting of k shapes and therefore use the last shape $\hat{h}_{t+k+1}$ in the predicted sequence to estimate the position of OSS interventional device 30 in the future time point.

Figure 9F:
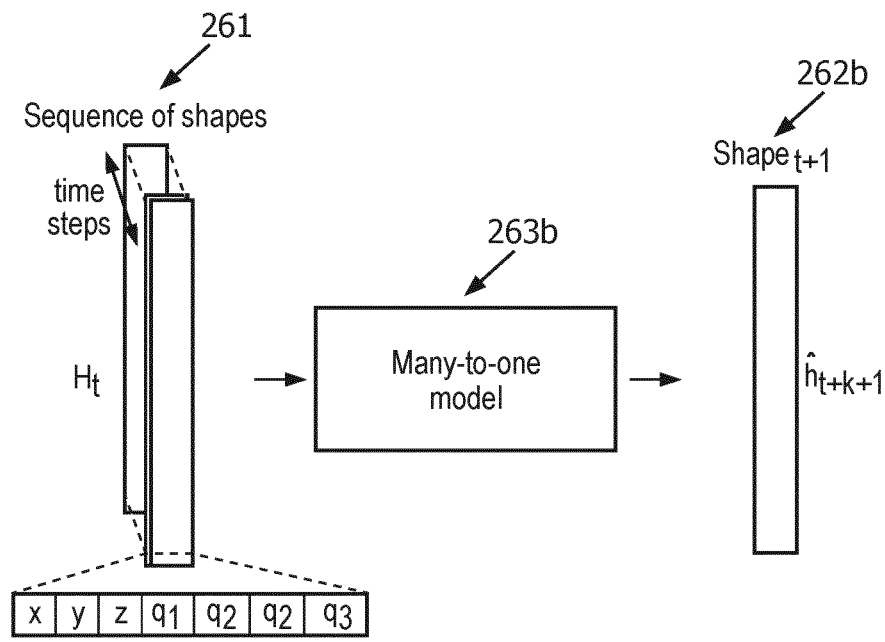

In an alternative embodiment as shown in FIG. 9F, forward predictive model 60*d* employs a many-to-one model 263*b* in lieu of sequence-to-sequence model 263*a* whereby the final layer will be the last shape $\hat{h}_{t+k+1}$.

Referring to FIG. 9C and FIG. 9D, a stage S92*e* of an exemplary interventional procedure 90*e* employing OSS guidewire 332 (FIG. 3F) and shape sensing controller 103 (FIG. 3F) and encompasses shape sensing controller 103 measure and storing a shape of OSS guidewire 332 during a navigation of an end-effector 340 to a target pose.

A stage S94*e* of procedure 90*e* involves shape sensing controller 103, forward predictive model 50*d* and a display controller 104. shape sensing controller 103 communicates a sequence 61d of k consecutive shapes to forward predictive model 60e to thereby inf infers the following sequence of shapes $\hat{H}_{t+1}$, where the last shape $\hat{h}_{t+k+1}$ is the predicted position of OSS guidewire 332. Display controller 104 controls a display of a sensed position image 105a of OSS guidewire 332 for guidance purposes to the end-effector 340 to the target pose.

Figure 10A:
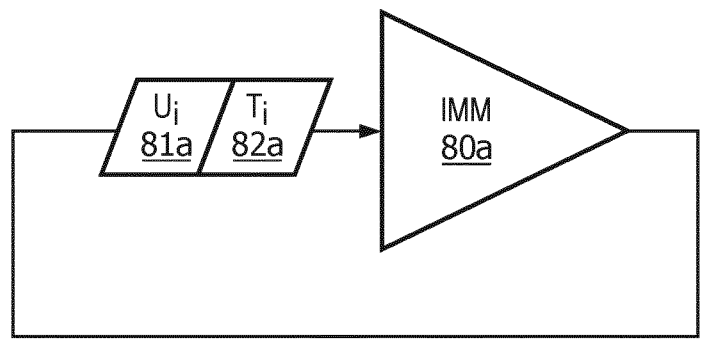
FIGS. 10A-10B illustrate first exemplary embodiments of an image predictive model and an image predictive method of the present disclosure
Figure 10B:
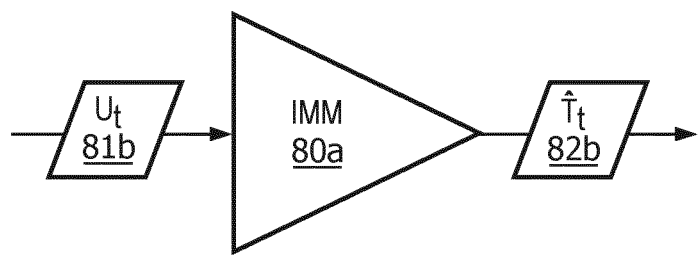

Referring to FIGS. 10A and 10B, an imaging predictive model 80a of the present disclosure is trained on expert data with reasonable coverage of different cases. This neural network 80a, given an ultrasound image 81b, infers the relative position 81b of this image 81b in respect to the reference anatomy. In result, a motion between a former pose of an end-effector and a current pose of an end-effector in the anatomy (e.g., a heart) may be calculated as will be further described herein.

FIG. 10A shows a batchwise training of the imaging predictive model 80a. During training, network constantly imaging predictive model 80a updates its weights using 2-tuples from the ground truth dataset consisting of ultrasound image and relative position of this image in respect to the reference anatomy.

FIG. 10B shows a real-time inference using imaging predictive model 80a that, given an image 81b, predicts the relative pose 82b of the end-effector n respect to the reference anatomy, (e.g., a reference ultrasound image).

In a training phase, as shown in FIG. 10A, a data acquisition controller (not shown) is configured to receive and interpret information from both a robot and end-effector (e.g., an ultrasound device), and save data on a data storage media (not shown) by a data acquisition controller (not shown) in a format defined by the following specifications: training dataset D consisting of i data points represented by a 2-tuple: $d_i=(U_i, T_i)$. This 2-tuple consists of an ultrasound image $U_i$ 81a that was acquired at a certain position $T \in SE(3)$ 82a in respect to the reference positon.

A training controller is configured to interpret the training dataset D saved on the data storage media. This dataset D consists of i data points represented by a 2-tuple: $d_i=(U_i, T_i)$. This 2-tuple consists of: ultrasound image $U_i$ 81a of the anatomy and relative motion $T_i$ 82a between current pose of the end-effector at which ultrasound image $U_i$ was acquired and some arbitrarily chosen reference position.

Figure 12A:
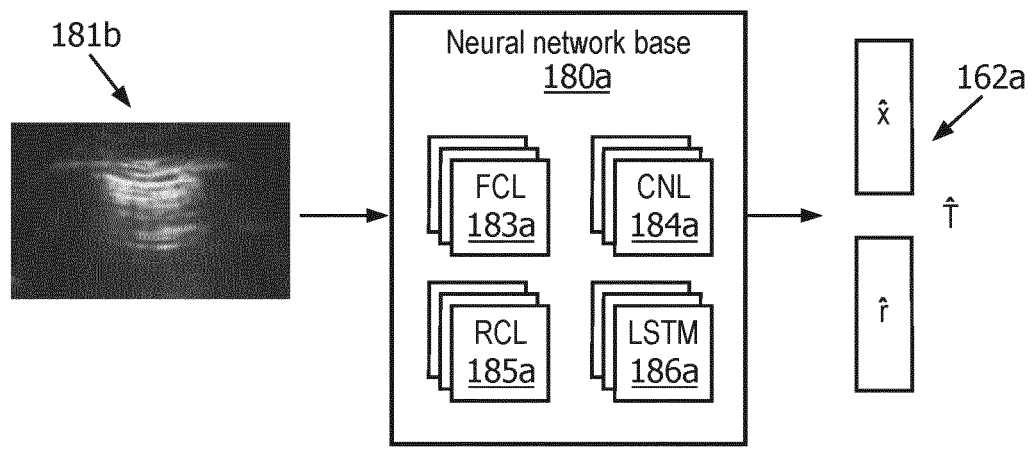
FIGS. 12A-12B illustrate third exemplary embodiments of a image predictive model and an image predictive method of the present disclosure.

In one embodiment as shown in FIG. 12A, image predictive model 80a employs a neural network base 180a including an input layer, hidden layers and an output layer derived from a combination of one or more fully connected layers (FCL) 183a, one or more convolutional layers (CNL) 184a, one or more recurrent layers (RCL) 185a, and one or more long term short memory (LSTM) layers 186a.

In practice, the combination of layers is configured to implement a relative positioning of image $U_C$ to a reference image to thereby pose $\hat{T}$.

In one embodiment for implementing a relative positioning of image $U_C$ to a reference image to thereby pose $\hat{T}$, neural network base 180a includes a set of N number of fully connected layers 183a.

In a second embodiment for implementing a relative positioning of image $U_C$ to a reference image to thereby pose $\hat{T}$, neural network base 180a includes a set of N convolutional layers 184a followed by either a set of M fully connected layers 183a or a set of W recurrent layers 185a or a set of W long term short memory layers 186a.

In a third embodiment for implementing a relative positioning of image $U_C$ to a reference image to thereby pose $\hat{T}$, neural network base 180a includes a set of N convolutional layers 184a followed combination of a set of M fully connected layers 183a and a set of W recurrent layers 185a or a set W of long term short memory layers 186a.

In practice, a fully connected layer 183a may include K neurons, where N, M, W, K may be any positive integer, and values may vary depending on the embodiments. For example, N may be about 8, M may be about 2, W may be about 2, and K can be about 1000. Also, a convolutional layer 184a may implement a non-linear transformation, which may be a composite function of operations (e.g., batch normalization, rectified linear units (ReLU), pooling, dropout and/or convolution), and a convolutional layer 184a may also include a non-linearity function (e.g. including rectified non-linear ReLU operations) configured to extract rectified feature maps.

Further in practice, one of the layers 183a or 184a serve as an input layer for inputting image $U_C$, and one of the layers 183a, 185a and 186a may serve as an output layer for outputting a pose 182a of end-effector 40 in Cartesian space (e.g., a translation and a rotation of the end-effector 40 in Cartesian space). The outputted pose of end-effector 40 in Cartesian space may be represented as vectorial parametrization and/or non-vectorial parametrization of a rigid-body position and orientation. More particularly, the parametrizations may be in the form of Euler angles, quaternions, matrix, exponential map, and/or angle-axis representing rotations and/or translations (e.g., including a direction and a magnitude for the translations).

Also in practice, the output layer may be a non-linear fully connected layer 183a that gradually shrinks a high-dimensional output of the last convolutional layer 184a of neural network base 180a to produce a set of output variables.

In training, training weights of image predictive model 80a are constantly updated by comparing a predicted relative motion of the end-effector ($\hat{T}$) in respect to some reference anatomy using image predictive model—given and ultrasound image 161c as input—with ground-truth relative motion T from a batch of training datasets D, which may be systematically or randomly selected from data memory (not shown). More particularly, the coefficients for the filters may be initialized with predefined or arbitrary values. The coefficients for the filters are applied to the batch of training datasets D via a forward propagation, and are adjusted via a backward propagation to minimize any output error.

Figure 11A:
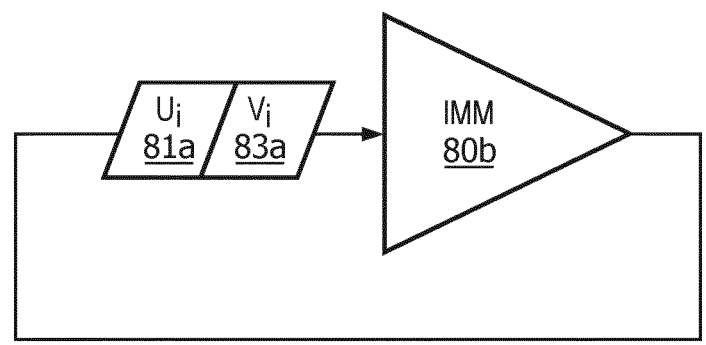
FIGS. 11A-11B illustrate second exemplary embodiments of an image predictive model and an image predictive method of the present disclosure.
Figure 11B:
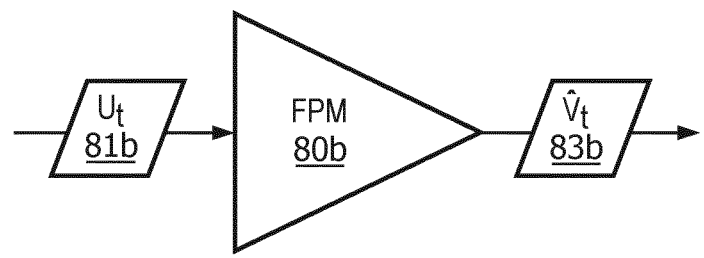

Referring to FIGS. 11A and 11B, an imaging predictive model 80b of the present disclosure is trained on expert data with reasonable coverage of different cases. This neural network 80b, given an ultrasound image 81b, infers the relative position 83b of this image 81b in respect to the reference anatomy. In result, a motion between a former pose of an end-effector and a current pose of an end-effector in the anatomy (e.g., a heart) may be calculated as will be further described herein.

FIG. 11A shows a batchwise training of the imaging predictive model 80b. During training, network constantly imaging predictive model 80b updates its weights using 2-tuples from the ground truth dataset consisting of ultrasound image and relative position of this image in respect to the reference anatomy.

FIG. 11B shows a real-time inference using imaging predictive model 80b that, given an image 81b, predicts 83b linear velocity and angular velocity of the end-effector with respect to the reference anatomy, (e.g., a reference ultrasound image).

In a training phase, shown in FIG. 11A, a data acquisition controller (not shown) is configured to receive and interpret information from both a robot and end-effector (e.g., an ultrasound device), and save data on a data storage media (not shown) by a data acquisition controller (not shown) in a format defined by the following specifications: training dataset D consisting of i data points represented by a 2-tuple: $d_i=(U_i, V_i)$. This 2-tuple consists of an ultrasound image $U_i$ 81*a* that was acquired at a certain position $T \in SE(3)$ in respect to the reference position via the vector 83*a* of linear velocity and angular velocity of the end-effector.

A training controller is configured to interpret the training dataset D saved on the data storage media. This dataset D consists of i data points represented by a 2-tuple: $d_i=(U_i, V_i)$. This 2-tuple consists of: ultrasound image $U_i$ 81*a* of the anatomy and relative n vector 83*a* of linear velocity and angular velocity of the end-effector at which ultrasound image $U_C$ was acquired and some arbitrarily chosen reference position.

Figure 12B:
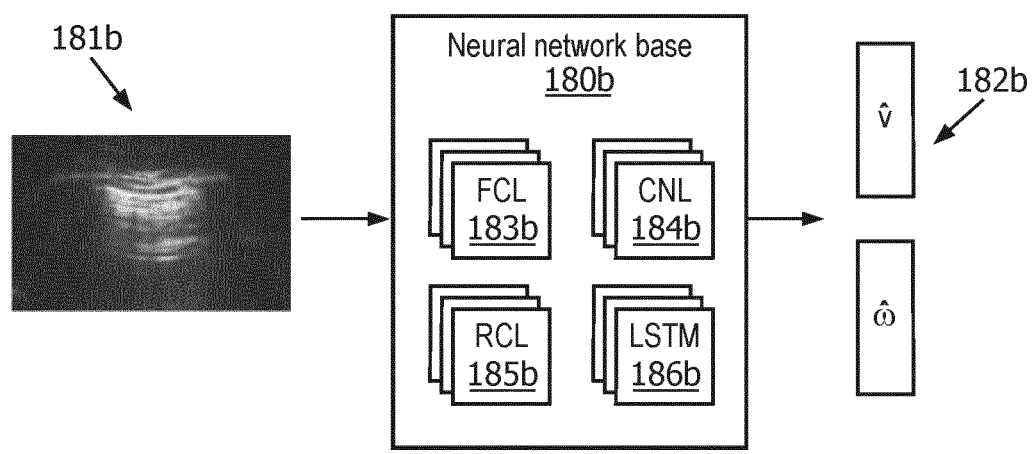

In one embodiment as shown in FIG. 12B, image predictive model 80*b* employs a neural network base 180*b* including an input layer, hidden layers and an output layer derived from a combination of one or more fully connected layers (FCL) 183*b*, one or more convolutional layers (CNL) 184*b*, one or more recurrent layers (RCL) 185*b*, and one or more long term short memory (LSTM) layers 186*b*.

In practice, the combination of layers is configured to implement a relative positioning of image $U_C$ to a reference image to thereby derive a linear velocity and/or an angular velocity of end-effector 40.

In one embodiment for implementing relative positioning of image $U_C$ to a reference image to thereby derive a linear velocity and/or an angular velocity of end-effector 40, neural network base 180*b* includes a set of N number of fully connected layers 183*b*.

In a second embodiment for implementing relative positioning of image $U_C$ to a reference image to thereby derive a linear velocity and/or an angular velocity of end-effector 40, neural network base 180*b* includes a set of N convolutional layers 184*b* followed by either a set of M fully connected layers 183*b* or a set of W recurrent layers 185*b* or a set of W long term short memory layers 186*b*.

In a third embodiment for implementing relative positioning of image $U_C$ to a reference image to thereby derive a linear velocity and/or an angular velocity of end-effector 40, neural network base 180*b* includes a set of N convolutional layers 184*b* followed combination of set of M fully connected layers 183*b* and a set of W recurrent layers 185*b* or a set W of long term short memory layers 186*b*.

In practice, a fully connected layer 183*b* may include K neurons, where N, M, W, K may be any positive integer, and values may vary depending on the embodiments. For example, N may be about 8, M may be about 2, W may be about 2, and K can be about 1000. Also, a convolutional layer 184*b* may implement a non-linear transformation, which may be a composite function of operations (e.g., batch normalization, rectified linear units (ReLU), pooling, dropout and/or convolution), and a convolutional layer 184*b* may also include a non-linearity function (e.g. including rectified non-linear ReLU operations) configured to extract rectified feature maps.

Further in practice, one of the layers 183*b* or 184*b* serve as an input layer for inputting image $U_C$, and one of the layers 183*b*, 185*b* and 186*b* may serve as an output layer for outputting a linear and angular velocity of the end effector $$\begin{bmatrix} \hat{v} \\ \hat{\omega} \end{bmatrix}$$

as regressed from last fully-connected layer (e.g. 6 units, 3 units for linear and 3 units for angular velocity) with linear or non-linear activation function.

In training, training weights of image predictive model 80*b* are constantly updated by comparing a predicted linear and angular velocity of the end-effector in respect to some reference anatomy—given ultrasound image 161*c* as input—with ground-truth end-effector linear and angular velocity describing motion to some reference anatomy from a batch of training datasets D, which may be systematically or randomly selected from data memory (not shown). More particularly, the coefficients for the filters may be initialized with predefined or arbitrary values. The coefficients for the filters are applied to the batch of training datasets D via a forward propagation, and are adjusted via a backward propagation to minimize any output error.

Figure 13A:
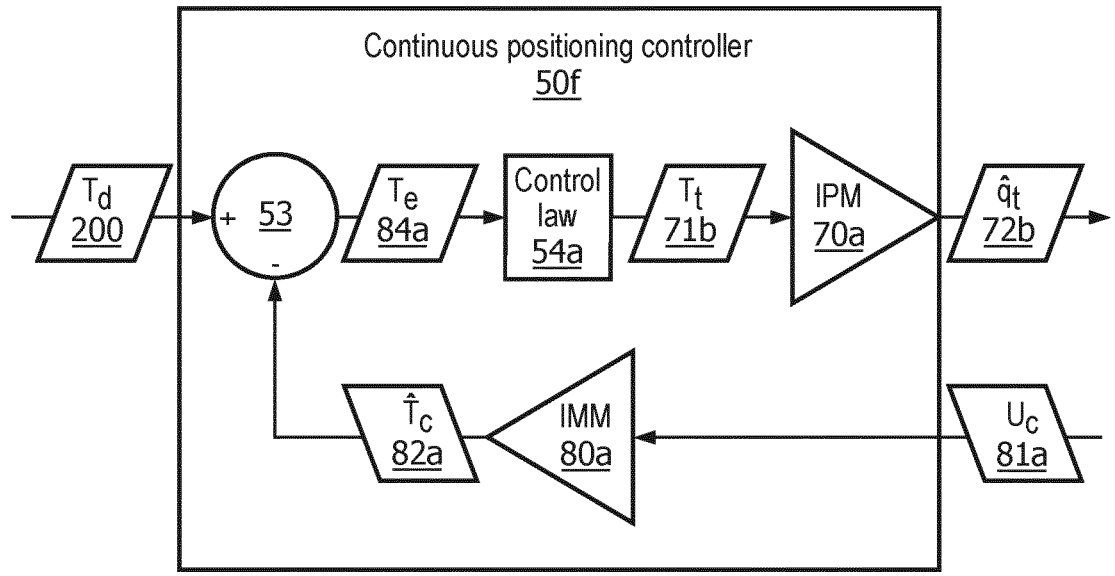
FIGS. 13A-13D illustrate a closed loop pose control of the present disclosure.
Figure 13B:
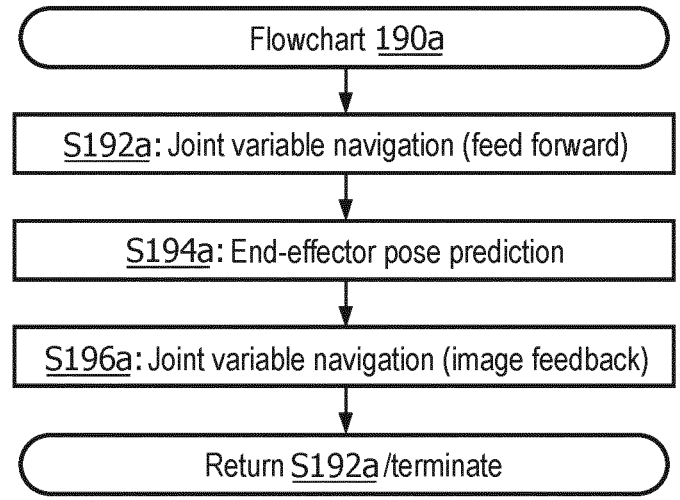

Referring to FIGS. 13A and 13B, a continuous positioning controller 50*f* employs inverse predictive model 70*a*, image predictive model 80*a*, a subtractor 53 and a control law 54*a* to execute a closed loop continuous position control method of the present disclosure as represented by flowchart 190*a*.

Figure 13C:
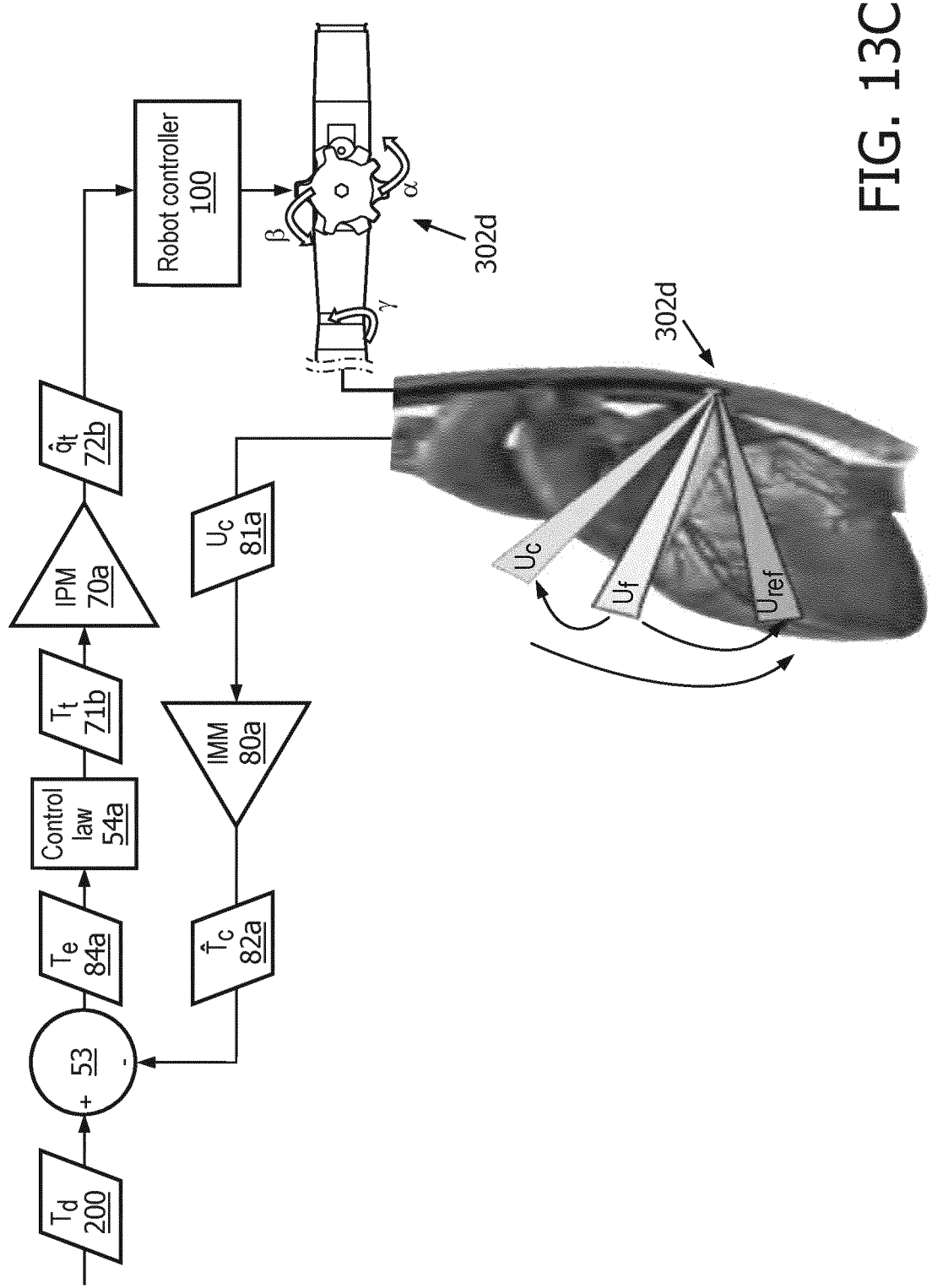

In one TEE probe embodiment, stage S192a of procedure 190*a* encompasses TEE probe handle 132 (FIG. 3A) being inserted into the robotic controller 100 (FIG. 3B) as known in the art of the present disclosure to controls the dials of handle 132 as well as a rotation of TEE probe 130. A TEE transducer 140 (FIG. 3A) is inserted into the body through the esophagus and positioned in the vicinity of the anatomical structure of interest, such as heart, for instance at a mid-esophageal position as shown in FIG. 13C. Ultrasound image parameters are defined at this target pose of TEE transducer 140.

A stage S194a of procedure 190*a* encompasses image predictive model 90 processing a current ultrasound image 81*a*, to which we will refer as former ultrasound image Up, to predict relative position of this image plane in respect to the reference anatomy $^{ref}\hat{T}_f$. Sonographer observes the anatomy using ultrasound image and decides about the desired movement of the transducer from its current position $T_d$. Alternatively, desired motion of the transducer could be provided from: external tracking devices, user interfaces, other imaging modalities that are registered to the ultrasound image, such as X-ray images that are registered to 3D TEE images using EchoNavigator (Philips).

Based on $T_d$, inverse predictive model 70*a* predicts joint variables $\hat{q}_t$ 72*a* that are required to move the robot to the desired position. Robot controller 100 receives the joint variables 72*a* and moves TEE probe 130 accordingly.

A stage S196a of procedures 190*a* encompasses the ultrasound transducer reaching another position at which ultrasound image $U_C$ is acquired. Image predictive model 90*g* uses process the current ultrasound image $U_C$ to predict relative position of both current image plane in respect to the reference anatomy $^{ref}\hat{T}_c$. In result a motion between former and current position in the anatomy, such as heart, can be calculated as follows:

$$^c\hat{T}_f = \left(^{ref}\hat{T}_c\right)^{-1} {}^{ref}\hat{T}_f.$$

Figure 13D:
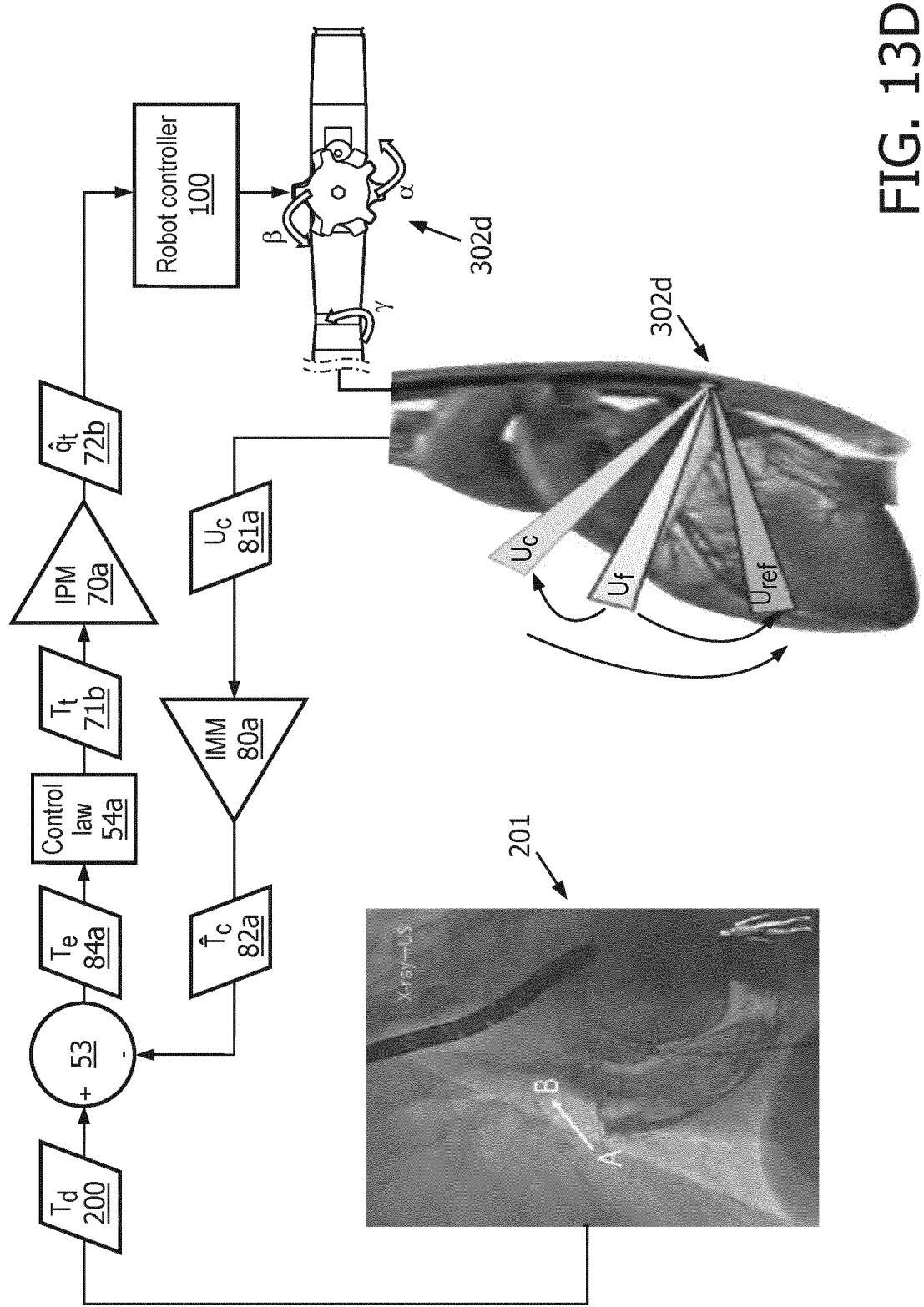

In a second TEE probe embodiment, as shown in FIG. 13D, a selection of a path on an image 201 generated by an external imaging modality registered to the ultrasound image may be utilized to determine the desired position $T_d$ (e.g., X-ray image, as well as cone-beam CT image can be registered to the ultrasound image using methods known in the art (Philips EchoNavigator)).

Figure 14A:
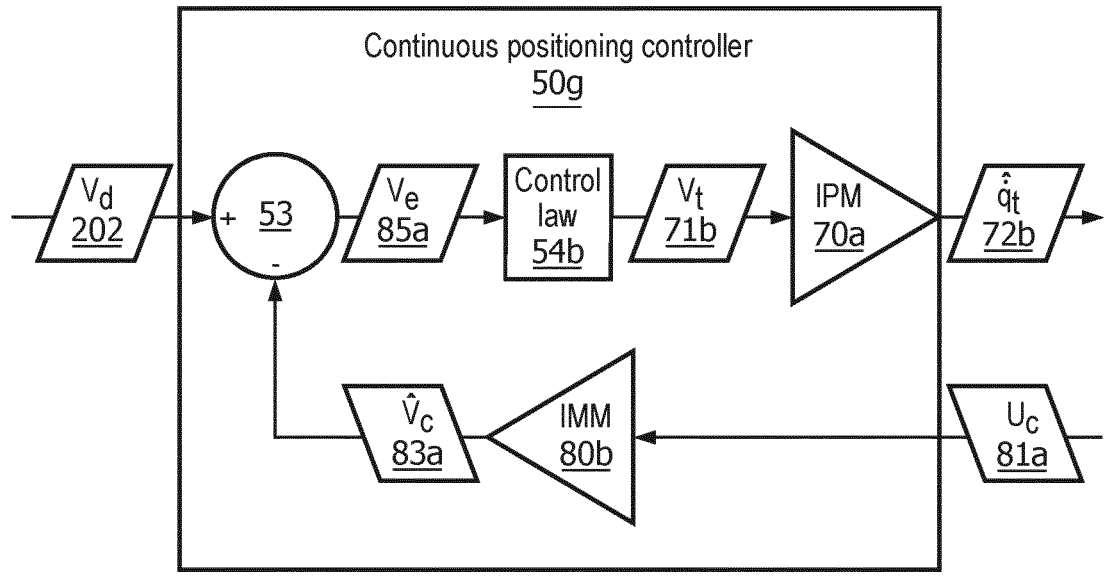
FIGS. 14A-14D illustrate a closed loop vector velocity control of the present disclosure.
Figure 14B:
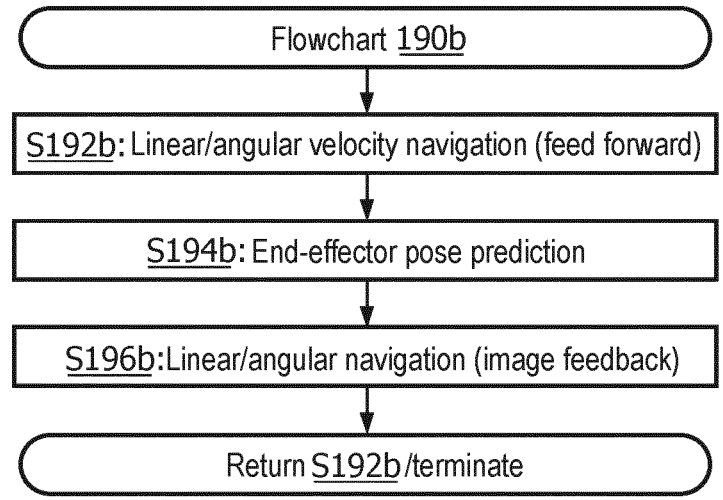

Referring to FIGS. 14A and 14B, a continuous positioning controller 50g employs inverse predictive model 70b, image predictive model 80b, a subtractor 53 and a control law 54b to execute a closed loop continuous position control method of the present disclosure as represented by flowchart 190b.

Figure 14C:
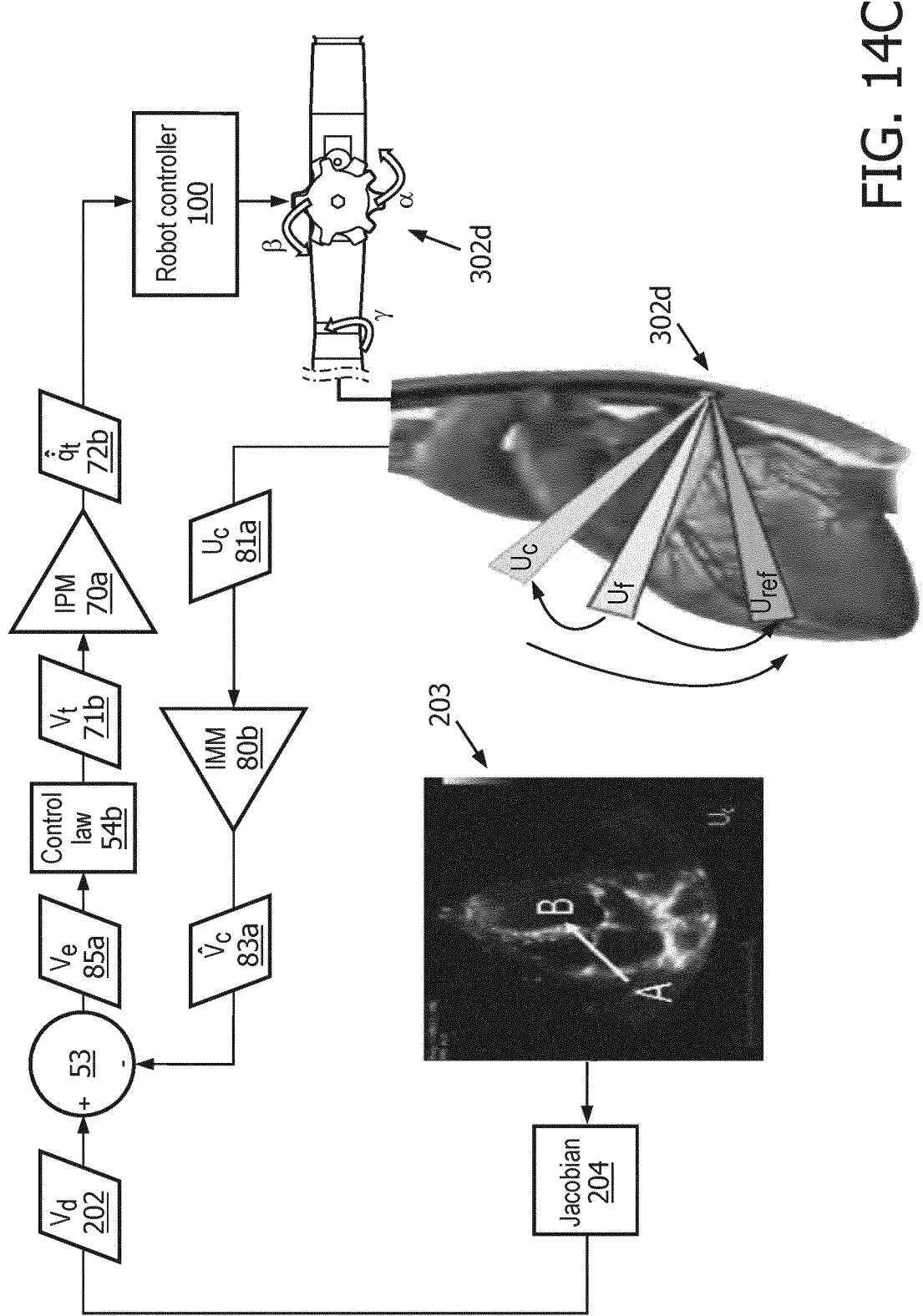
Figure 14D:
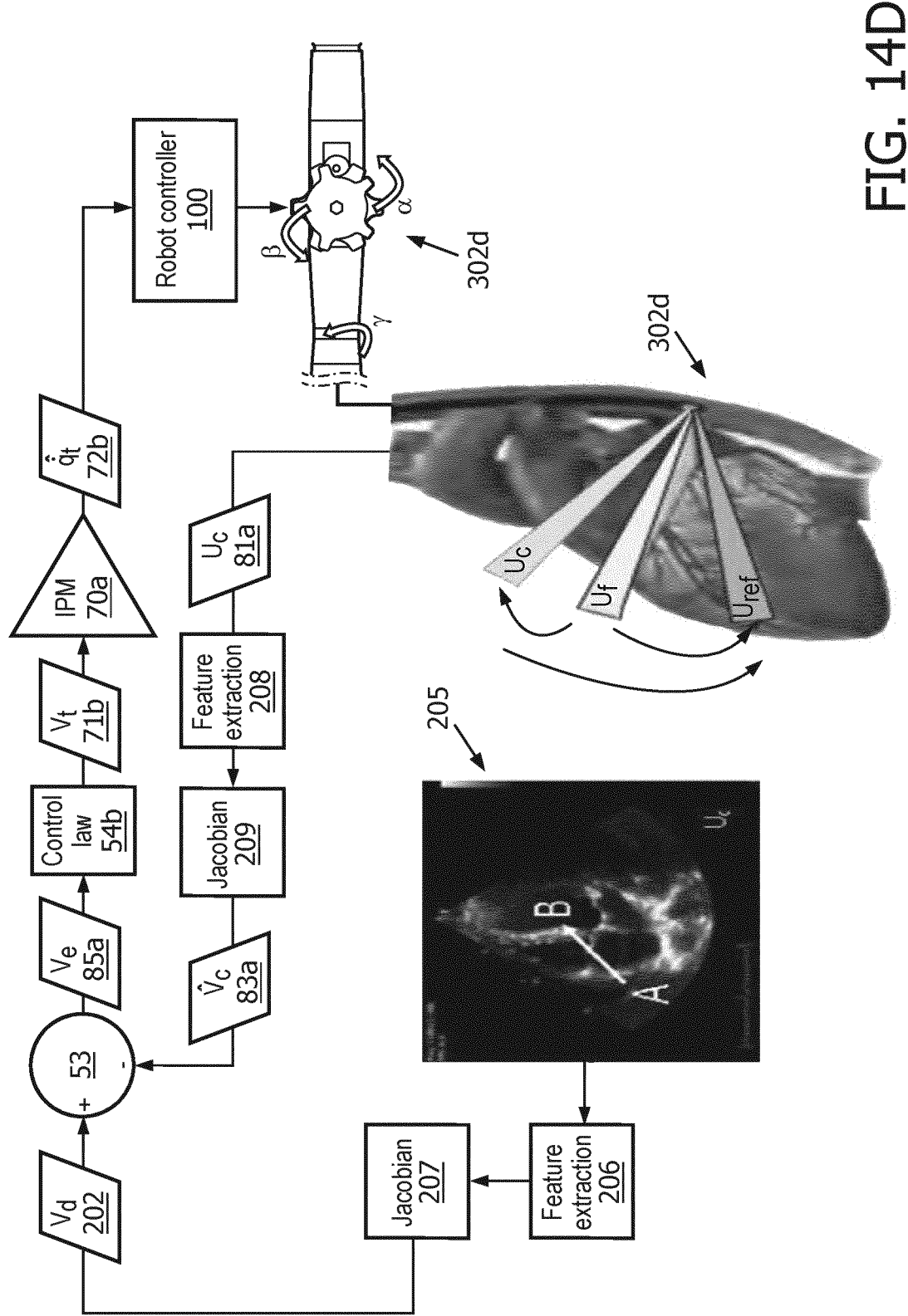

In one TEE probe embodiment, stage S192b of procedure 190b encompasses TEE probe handle 142 (FIG. 3A) being inserted into the robotic controller 100 (FIG. 3B) as known in the art of the present disclosure to controls the dials of handle 142 as well as a rotation of TEE probe 140. A TEE transducer 140 (FIG. 3A) is inserted into the body through the esophagus and positioned in the vicinity of the anatomical structure of interest, such as heart, for instance at a mid-esophageal position as shown in FIG. 14C. Ultrasound image parameters are defined at this target pose of TEE transducer 140

A stage S194b of procedure 190b encompasses a user desiring to move the transducer in the image space for instance by selecting the path from point A to point B in ultrasound image 203 or a transformation between image plane A and B. In this embodiment, a first linear and angular velocity 202 defined by the path on the image is transformed to the end effector coordinate system using $^{end\text{-}effector}J_{image}$ Jacobian 204, which is calculated by knowing the spatial relationship between end effector and image coordinate system using methods known in art of the present disclosure.

Based on $V_d$, inverse predictive model 70b (FIG. 7B) predicts joint velocities $\dot{q}_r$ 72b that are required to move the robot to the desired position. Robot controller 100 receives the joint velocities $\dot{q}_r$ 72b and moves TEE probe 130 accordingly.

A stage S196b of procedures 190a encompasses the ultrasound transducer reaching another position at which ultrasound image $U_C$ is acquired. Image predictive model 80b process the current ultrasound image $U_C$ 81a to predict a velocity vector 83a of the end-effector between points A and B. The image predictive model 80b estimating the function between Cartesian velocity of the end effector and the velocities in the joint space, i.e. neural network models a manipulator Jacobian—given a 6-vector consisting of the linear and angular velocities of the end effector 71c to predict n-vector 72c of joint velocities.

As understood by those skilled in the art of the present disclosure, neural networks that model spatial relationships between images of the anatomy, such as heart, require large training dataset, which are specific to given organ.

In an alternative embodiment, features are directly extracted from the images in order to validate the position of the transducer. In this embodiment as shown in FIG. 14C, a user selects the object on the image 205, e.g. apical wall, around which system will extract certain salient features via a feature extraction 206. These features, which may include edges, shape, and size of the object, are first detected using methods know in the art of the present disclosure (e.g. Canny edge detector, morphological operation, etc.), and second tracked using scale invariant feature transform (SIFT) that is known in the art of the present disclosure. Finally system defines a path between selected object and the center of the field of view, which indicates the required motion on the image. By tracking the salient features using SIFT, continuous position controller 50g (FIG. 14A) can correct the predictions from the network within the close-loop control.

More particular, a velocity-based control system of the continuum-like robot. Desired motion on the image is identified as soon as the user selects certain object on the image, e.g. apical wall (see red dot on the ultrasound image). Motion is defined by a path between center of the field of view and the selected object, which can be transformed to linear and angular velocities in the end effector space using Jacobian 204. This Cartesian velocity is then sent to the neural network which will infer joint velocities. Achieved position will be iteratively validated against the path defined by a constantly tracked object, and center of the field of view.

In practice, the closed control loop of FIGS. 13 and 14 may closed using other modalities, such as optical shape sensing (OSS), electromagnetic tracking, or X-ray images registered to the ultrasound images using for instance Philips EchoNavigator.

Also in practice, prediction accuracy of the neural network can be affected by the configuration of the flexible endoscope. Thus, a position of a transducer in respect to heart is first defined, using for instance neural network g, or Philips HeartModel, which will implicitly define one of the possible configurations. Second, a certain set of network weights will be loaded into the models according to the detected configuration, thus improving the prediction accuracy.

Similar approach can be used to guide the user to the location at which the most optimal images and guidance can be provided.

Furthermore, one of the hardest issues in machine/deep learning is the accessibility of large data in the right format for training of the predictive models. More particularly, collecting and constructing the training and validation sets is very time consuming and expensive because it requires domain-specific knowledge. For instance, to train a predictive model to accurately differentiate a benign breast tumor and a malignant breast tumor, such training needs several thousands of ultrasound images annotated by expert radiologists and transformed into a numerical representation that a training algorithm can understand. Additionally, the image datasets might be inaccurate, corrupted or labelled with noise, all leading to detection inaccuracies, and an acquisition of large medical datasets may trigger ethical and privacy concerns, and many others concerns.

Figure 15:
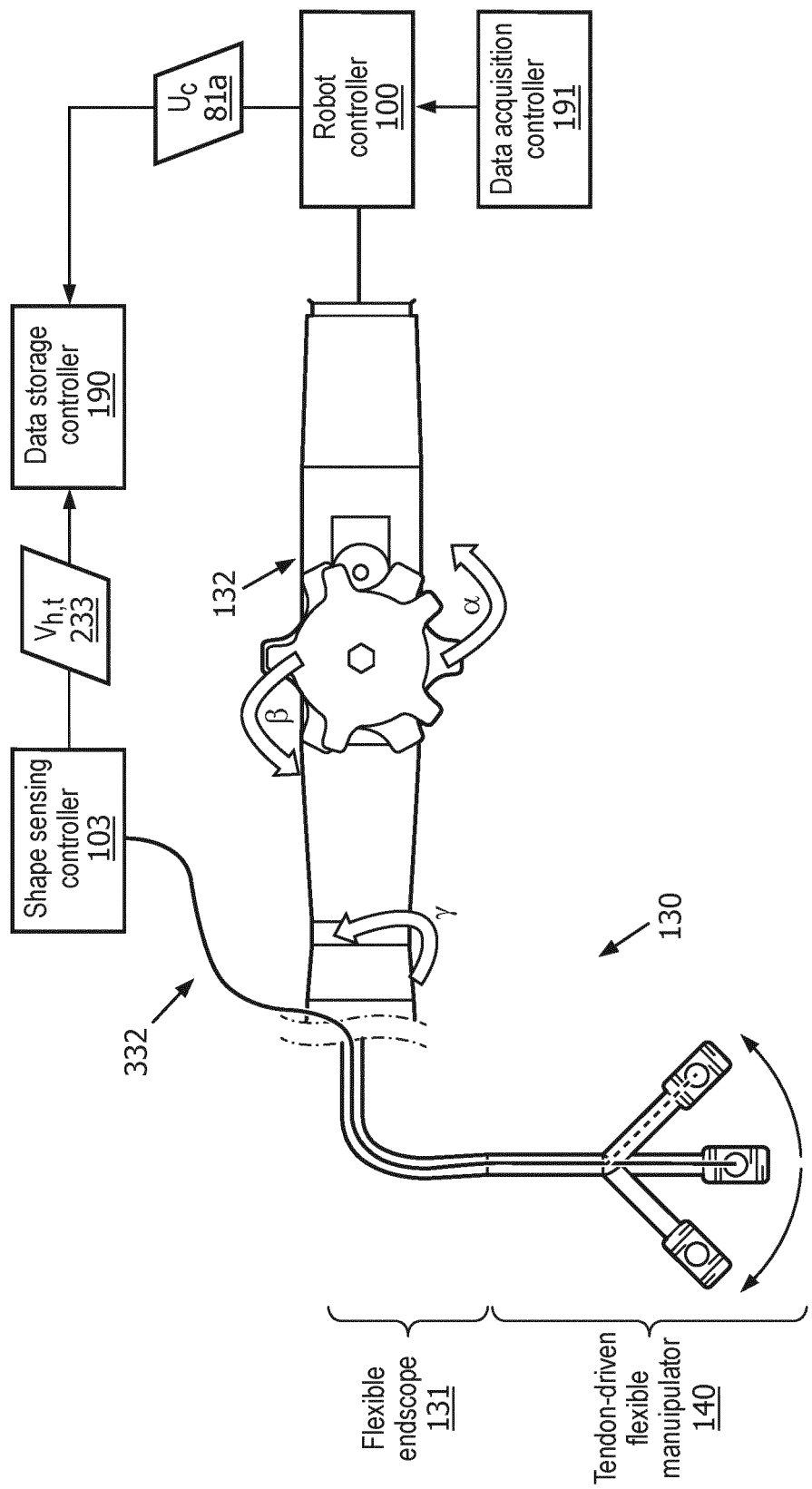

Referring to FIG. 15, a training data collection system of the present disclosure employs a shape sensing controller 103 providing 3D position vectors 233 for each point on the optical shape sensing fiber 332 that is mounted to both endoscope 131 and tendon-driven manipulator 231 of the robot. A distal part of the optical fiber 332 is embedded in the plastic case which rigidly connects optical fiber to the end-effector and introduce a certain curvature within the shape.

For example, FIGS. 16A and 16B show a distal end 332d of an optical shape sensing fiber 332 embedded in the plastic casing 350 that is rigidly attached to an ultrasound transducer 232 of manipulator 231 as shown in FIGS. 16C and 16D. The plastic casing 350 reinforces a certain curvature in the shape thus enabling estimation of the end-effector pose using template matching algorithm as known in the art of the present disclosure (e.g., a data acquisition sequence 370 as shown in FIG. 17 with an alpha and beta on each axis corresponds to knobs positions on the TEE handle 132 shown in FIG. 15).

Referring back to FIG. 16, generally, by detecting this pattern one can estimate the pose $T \in SE(3)$ of the end-effector using methods known in art. A robot controller 100 sends motion commands to the robot, which controls actuated knobs responsible for pulling or loosening the tendons.

By altering the state of the tendons, the position of the end-effector is changed as shown on in FIGS. 3D and 3E. A data storage controller 190 receives shape $h \in (p_1 \ldots p_n)$ of optical fiber, pose T of the end-effector as well as motion commands, i.e. joint positions $q_t$, from shape sensing and robot controller respectively. Data is stored as a 3-tuple on the storage device and used later on for training of the deep convolutional neural network of the present disclosure More particular, a shape-sensed guidewire 332 is embedded or attached to the continuum robot, which uses an optical shape sensing (OSS) technology known in the art. OSS uses light along a multicore optical fiber for device localization and navigation during surgical intervention. The principle involved makes use of distributed strain measurements in the optical fiber using characteristic Rayleigh backscatter or controlled grating patterns.

Shape sensing controller 103 is configured to acquire the shape of shape-sensed guidewire 322, estimate the pose $T \in SE(3)$ of the end-effector that is rigidly attached to a plastic casing 350, which enforces a certain curvature in the guidewire as previously describe herein. The methods for estimating pose T based on a well-defined curvature as well as template matching algorithm as known in the art of the present disclosure.

Data acquisition controller 191 is configured to generate a sequence of motor commands according to pre-defined acquisition pattern (e.g., a spiral, radial, or square motion, etc.) and send movement commands to robot controller 100.

Robot controller 100 is configured to receive robot position and send movement signals to the robot. Using motorized knobs robot will pull/loosen the tendons, which will result in the motion of the end-effector. Robot controller is further configured to receive and interpret information from the data acquisition controller 191, and change the robot position based on the information from the data acquisition controller 191.

Data storage controller 190 is configured to receive and interpret information from both robot controller 100 and shape sensing controller 103, and save data on the data storage media (not shown) in a format defined by the following specifications:

First specification is to acquire training dataset D for all configurations pre-defined by the data acquisition controller 191. A dataset D consists of a set of n sequences W: $D=\{W_1, W_2, \ldots W_n\}$, each sequence $W_n$ consists of i data points $d_i$: $W_n=\{d_1, d_2, \ldots, d_i\}$; and each data point $d_i$ from the sequence is defined by a 3-tuple: $d_i=(T_i, H_i, Q_i)$ The 3-tuple consists of end-effector pose $T \in SE(3)$, sequence of k consecutive shapes such as $H \in (h_t, h_{t+1} \ldots h_{t+k})$, where $h \in (p_1 \ldots p_m)$ is a set of m vectors $p_m$ that describe both the position of the shape-sensed guidewire in 3D Euclidean space and auxiliary shape parameters such as strain, curvature, and twist, and a sequence of j consecutive joint variables $Q \in (q_t, q_{t+1} \ldots q_{t+j})$ acquired at time points starting from t to t+j. For instance, entry $q_t$ could be an angle on the control knobs $\alpha$, $\beta$ acquired at a time point t.

Figure 19:
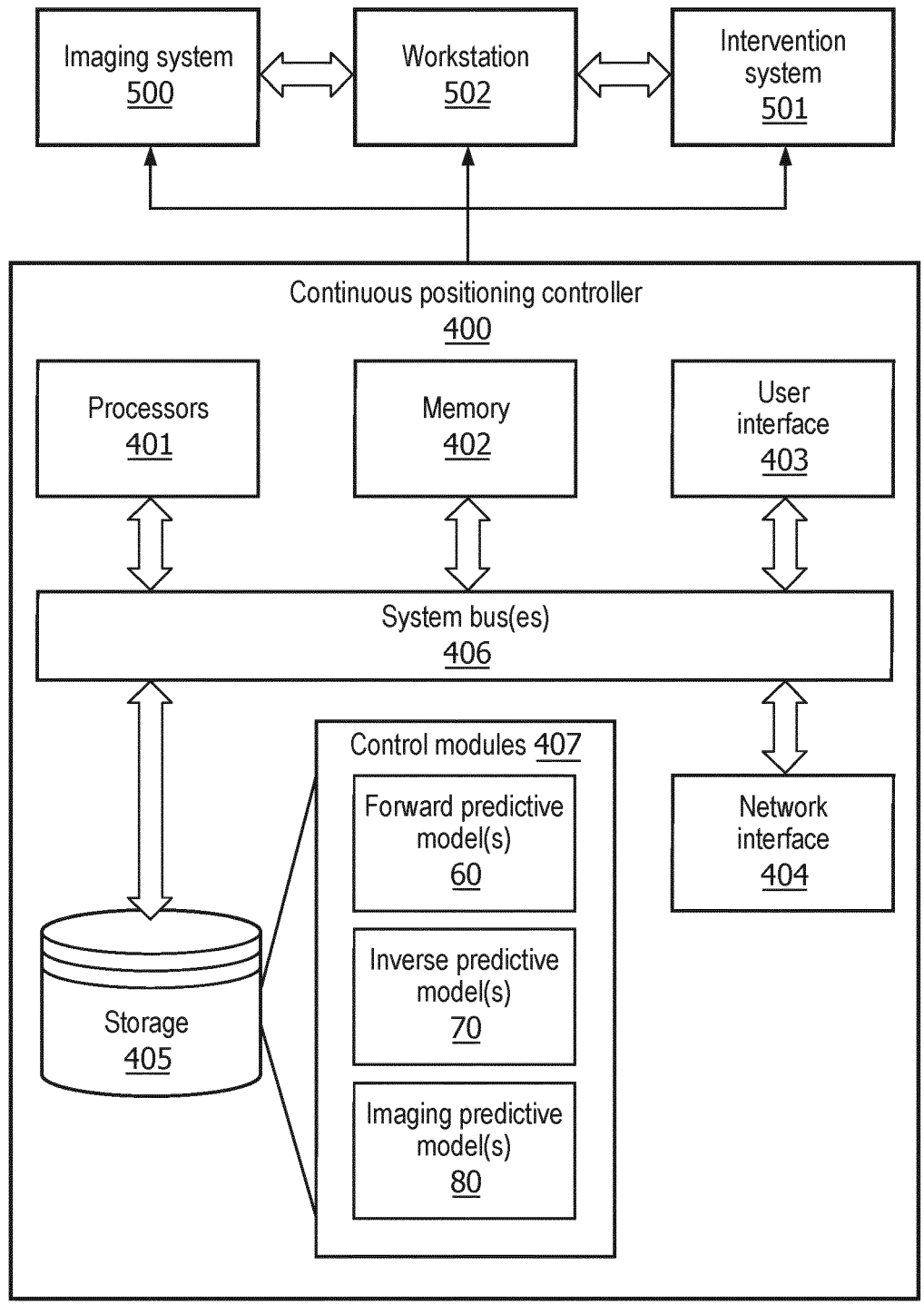
FIG. 19 illustrates an exemplary embodiment of a continuous positioning controller of the present disclosure.

Referring to FIG. 19, a training data collection method 360 of the present disclosure is executed by the training data collection system of FIG. 15.

Referring to both FIGS. 15 and 19, a stage S362 of method 360 encompasses the robot being moved to a home position by a robot controller 100 using for instance limit switches or proximity sensors. A distal part of the shape-sensed guidewire 232 is inserted in the indent 353 provided in the plastic casing 350. This indent 353 will enforce a certain curvature in the shape.

Casing 350 is rigidly attached to the end-effector of the continuum-like robot.

By using template matching algorithm as known in the art of the present disclosure during a stage S364 of method 360, shape sensing controller 103 can now estimate the pose $T \in SE(3)$ of the end-effector. Preferably, the coordinate system of the end-effector is defined by the template, however additional calibration matrixes can be used. When robotic system is still in the home position, pose of the end-effector is acquired in the OSS coordinate system. Every following pose that is acquired during the experiment is estimated relative to this initial position.

Data acquisition controller 191 generates a motion sequence, i.e. set of joint variables, according to pre-defined acquisition pattern (e.g., pattern 370 of FIG. 18). Motion sequence is sent iteratively by data acquisition controller 191 to the robot controller 100 that moves the robot according to the generated joint variables.

Stage S366 of method 300 encompasses, at each time point, an acquisition and storage of a data tuple $d_i=(T_i, H_i, Q_i)$ the data storage controller 190. Of importance, because $H_i$ and $Q_i$ are sequential, all former time points are kept in the memory by the data storage controller 190.

To facilitate a further understanding of the various inventions of the present disclosure, the following description of FIG. 19 teaches an exemplary embodiment of a continuous positioning controller of the present disclosure. From this description, those having ordinary skill in the art will appreciate how to apply various aspects of the present disclosure for making and using additional embodiments of continuous positioning controller of the present disclosure.

Referring to FIG. 19, a continuous positioning controller 400 includes one or more processor(s) 401, memory 402, a user interface 403, a network interface 404, and a storage 405 interconnected via one or more system buses 406.

Each processor 401 may be any hardware device, as known in the art of the present disclosure or hereinafter conceived, capable of executing instructions stored in memory 402 or storage or otherwise processing data. In a non-limiting example, the processor(s) 401 may include a microprocessor, field programmable gate array (FPGA), application-specific integrated circuit (ASIC), or other similar devices.

The memory 402 may include various memories, e.g. a non-transitory and/or static memory, as known in the art of the present disclosure or hereinafter conceived, including, but not limited to, L1, L2, or L3 cache or system memory. In a non-limiting example, the memory 402 may include static random access memory (SRAM), dynamic RAM (DRAM), flash memory, read only memory (ROM), or other similar memory devices.

The user interface 403 may include one or more devices, as known in the art of the present disclosure or hereinafter conceived, for enabling communication with a user such as an administrator. In a non-limiting example, the user interface may include a command line interface or graphical user interface that may be presented to a remote terminal via the network interface 404.

The network interface 404 may include one or more devices, as known in the art of the present disclosure or hereinafter conceived, for enabling communication with other hardware devices. In a non-limiting example, the network interface 404 may include a network interface card (NIC) configured to communicate according to the Ethernet protocol. Additionally, the network interface 404 may implement a TCP/IP stack for communication according to the TCP/IP protocols. Various alternative or additional hardware or configurations for the network interface 404 will be apparent.

The storage 405 may include one or more machine-readable storage media, as known in the art of the present disclosure or hereinafter conceived, including, but not limited to, read-only memory (ROM), random-access memory (RAM), magnetic disk storage media, optical storage media, flash-memory devices, or similar storage media. In various non-limiting embodiments, the storage 405 may store instructions for execution by the processor(s) 401 or data upon with the processor(s) 401 may operate. For example, the storage 405 may store a base operating system for controlling various basic operations of the hardware. The storage 405 also stores application modules in the form of executable software/firmware for implementing the various functions of the controller 400a as previously described in the present disclosure including, but not limited to, forward predictive model(s) 60, inverse predictive model(s) 70 and imaging predictive model(s) 80 as previously described in the present disclosure.

In practice, controller 400 may be installed within an X-ray imaging system 500, an intervention system 501 (e.g., an intervention robot system), or a stand-alone workstation 502 in communication with X-ray imaging 500 system and/or intervention system 501 (e.g., a client workstation or a mobile device like a tablet). Alternatively, components of controller 400 may be distributed among X-ray imaging system 500, intervention system 501 and/or stand-alone workstation 502.

Also in practice, additional controllers of the present disclosure including a shape sensing controller, a data storage controller and a data acquisition controller may also each include one or more processor(s), memory, a user interface, a network interface, and a storage interconnected via one or more system buses as arranged in FIG. 19, whereby the storage contains applicable application modules of that controller as previously described herein. Alternatively, two or more controllers of the present disclosure may be integrated as a single controller, where the storage contains applicable application modules of the two or more controllers as previously described herein.

Referring to FIGS. 1-19, those having ordinary skill in the art of the present disclosure will appreciate numerous benefits of the present disclosure.

Further, as one having ordinary skill in the art will appreciate in view of the teachings provided herein, structures, elements, components, etc. described in the present disclosure/specification and/or depicted in the Figures may be implemented in various combinations of hardware and software, and provide functions which may be combined in a single element or multiple elements. For example, the functions of the various structures, elements, components, etc. shown/illustrated/depicted in the Figures can be provided through the use of dedicated hardware as well as hardware capable of executing software in association with appropriate software for added functionality. When provided by a processor, the functions can be provided by a single dedicated processor, by a single shared processor, or by a plurality of individual processors, some of which can be shared and/or multiplexed. Moreover, explicit use of the term "processor" or "controller" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Having described preferred and exemplary embodiments of the various and numerous inventions of the present disclosure (which embodiments are intended to be illustrative and not limiting), it is noted that modifications and variations can be made by persons skilled in the art in light of the teachings provided herein, including the Figures. It is therefore to be understood that changes can be made in/to the preferred and exemplary embodiments of the present disclosure which are within the scope of the embodiments disclosed herein.

Moreover, it is contemplated that corresponding and/or related systems incorporating and/or implementing the device/system or such as may be used/implemented in/with a device in accordance with the present disclosure are also contemplated and considered to be within the scope of the present disclosure. Further, corresponding and/or related method for manufacturing and/or using a device and/or system in accordance with the present disclosure are also contemplated and considered to be within the scope of the present disclosure.

The invention claimed is:

1. A positioning controller for an interventional device, the positioning controller comprising:
   a memory storing:
      an imaging predictive model configured with kinematics of the interventional device to receive imaging data and to output data related to a prediction of a navigated pose of the interventional device, and
      a control predictive model configured with kinematics of the interventional device to receive error positioning data and to output data related to a prediction of a corrective positioning motion of the interventional device,
   wherein the interventional device includes an imaging device and at least one joint; and
   at least one processor in communication with the memory, the at least one processor configured to:
      apply the imaging predictive model to imaging data generated by the imaging device of the interventional device to predict a navigated pose of a portion of the interventional device associated with the imaging device, generate error positioning data derived based on a differential aspect between a target pose of the portion of the interventional device associated with the imaging device and the predicted navigated pose of the portion of the interventional device associated with the imaging device, wherein the error positioning data comprises at least one velocity for the portion of the interventional device associated with the imaging device, apply the control predictive model to the generated error positioning data to predict a corrective positioning motion of the interventional device, wherein the predicted corrective positioning motion comprises one or more joint velocities for the at least one joint, the one or more joint velocities derived, by the control predictive model, based on the at least one velocity for the portion of the interventional device associated with the imaging device, and generate positioning commands that control a corrective positioning of the portion of the interventional device associated with the imaging device to the target pose based on the predicted corrective positioning motion.

2. The positioning controller of claim 1, wherein at least one of:

the imaging predictive model is trained on a correlation of a relative imaging by the imaging device and forward kinematics of the interventional device, and the control predictive model is an inverse predictive model is trained on inverse kinematics of the interventional device.

3. The positioning controller of claim 2, wherein the inverse predictive model is further trained based on at least one auxiliary navigation parameter of the interventional device that is auxiliary to the inverse kinematics of the interventional device predictive of the corrective positioning motion of the interventional device; and wherein the at least one processor is further configured to apply the inverse predictive model to both the error positioning data and the at least one auxiliary navigation parameter of the interventional device to predict the corrective positioning motion of the interventional device.

4. The positioning controller of claim 1, wherein the portion of the interventional device associated with the imaging device comprises an end-effector.

5. The positioning controller of claim 1, wherein the at least one processor is further configured to generate the positioning commands continuously.

6. The positioning controller of claim 1, wherein the imaging predictive model includes:

a neural network having an input layer configured to input the imaging data generated by the imaging device, and an output layer configured to output at least one of a translation, a rotation, and a pivoting of the interventional device relative to a position of the interventional device in a reference image, wherein the neural network is configured to infer the predicted navigated pose of the portion of the interventional device associated with the imaging device based on at least one of the translation, the rotation, and the pivoting of the interventional device.

7. The positioning controller of claim 1, wherein the imaging predictive model includes:

a neural network having an input layer configured to input the imaging data generated by the imaging device, and an output layer configured to output at least one of a linear velocity and an angular velocity of the interventional device relative to a position of the interventional device in a reference image, wherein the neural network is configured to infer the predicted navigated pose of the portion of the interventional device associated with the imaging device based on the at least one of the linear velocity and the angular velocity of the interventional device.

8. The positioning controller of claim 1, wherein the imaging predictive model is configured to:

track a motion of features in the imaging data generated by the imaging device; and output at least one of a linear velocity and an angular velocity of the interventional device derived from a Jacobian transformation of the tracked motion of features in the imaging data, wherein the neural network is configured to infer the predicted navigated pose of the portion of the interventional device associated with the imaging device based on the at least one of the linear velocity and the angular velocity of the interventional device.

9. The positioning controller of claim 8, wherein the imaging predictive model is further configured to:

detect the features from the imaging data generated by the imaging device; and track the motion of the detected features.

10. The positioning controller of claim 1, wherein the control predictive model includes:

a neural network having an input layer configured to input the error positioning data derived from a differential pose between the target pose of the portion of the interventional device associated with the imaging device and the predicted navigated pose of the portion of the interventional device associated with the imaging device, and an output layer configured to output at least one of a translation, a rotation, and a pivoting of the interventional device derived from a regression of the differential pose between the target pose of the portion of the interventional device associated with the imaging device and the predicted navigated pose of the portion of the interventional device associated with the imaging device, wherein the neural network is configured to infer the predicted corrective positioning motion of the interventional device based on the at least one of the translation, the rotation, and the pivoting of the interventional device.

11. The positioning controller of claim 1, wherein the control predictive model includes:

a neural network having an input layer configured with the error positioning data derived from a differential motion between at least one of a linear velocity and an angular velocity of the portion of the interventional device associated with the imaging device and at least one of a predicted linear velocity and a predicted angular velocity of the portion of the interventional device associated with the imaging device, and an output layer configured to output the one or more joint velocities of the interventional device from a regression of the differential motion between the at least one of the linear velocity and the angular velocity of the portion of the interventional device associated with the imaging device and the at least one of the predicted linear velocity and the predicted angular velocity of the portion of the interventional device associated with the imaging device.

12. The positioning controller of claim 1,
wherein the control predictive model is configured to further receive at least one auxiliary navigation parameter of the interventional device, and further process the at least one auxiliary navigation parameter to output the predicted corrective positioning motion of the interventional device; and
wherein the at least one processor is further configured to apply the control predictive model to both the error positioning data and the at least one auxiliary navigation parameter of the interventional device to predict the corrective positioning motion of the interventional device.

13. A non-transitory computer-readable storage medium having stored a computer program comprising instructions, which, when executed by a processor, cause the processor to:
apply an imaging predictive model to imaging data generated by an imaging device of an interventional device to predict a navigated pose of a portion of the interventional device associated with the imaging device, wherein the imaging predictive model is configured with kinematics of the interventional device to receive the imaging data and to output the predicted navigated pose of the interventional device;
generate an error positioning data derived from a differential aspect between a target pose of a portion of the interventional device associated with the imaging device and the predicted navigated pose of the portion of the interventional device associated with the imaging device, wherein the error positioning data comprises at least one velocity for the portion of the interventional device associated with the imaging device,
apply a control predictive model to the error positioning data to predict a corrective positioning motion of the interventional device, wherein the control predictive model is configured with kinematics of the interventional device to receive the error positioning data and to output the predicted corrective positioning motion of the interventional device,
wherein the predicted corrective positioning motion comprises one or more joint velocities for at least one joint of the interventional device, the one or more joint velocities derived, by the control predictive model, based on the at least one velocity for the portion of the interventional device associated with the imaging device; and
generate positioning commands that control a corrective positioning by the interventional device of the portion of the interventional device associated with the imaging device to the target pose based on the predicted corrective positioning motion of the interventional device.

14. The non-transitory computer-readable storage medium of claim 13, wherein the imaging predictive model includes:
a neural network having an input layer configured to input the imaging data generated by the imaging device, and an output layer configured to output at least one of a translation, a rotation, and a pivoting of the interventional device relative to a position of the interventional device in a reference image,
wherein the neural network is configured to infer the predicted navigated pose of the portion of the interventional device associated with the imaging device based on at least one of the translation, the rotation, and the pivoting of the interventional device.

15. The non-transitory computer-readable storage medium of claim 13, wherein the imaging predictive model includes:
a neural network having an input layer configured to input the imaging data generated by the imaging device, and an output layer configured to output at least one of a linear velocity and an angular velocity of the interventional device relative to a position of the interventional device in a reference image,
wherein the neural network is configured to infer the predicted navigated pose of the portion of the interventional device associated with the imaging device based on the at least one of the linear velocity and the angular velocity of the interventional device.

16. The non-transitory computer-readable storage medium of claim 13, wherein the control predictive model includes:
a neural network having an input layer configured with the error positioning data derived from a differential motion between at least one of a linear velocity and an angular velocity of the portion of the interventional device associated with the imaging device and at least one of a predicted linear velocity and a predicted angular velocity of the portion of the interventional device associated with the imaging device, and an output layer configured to output the one or more joint velocities of the interventional device from a regression of the differential motion between the at least one of the linear velocity and the angular velocity and the at least one of the predicted linear velocity and the predicted angular velocity.

17. A positioning method for an interventional device including an imaging device, the method comprising
applying an imaging predictive model to imaging data generated by the imaging device to predict a navigated pose of a portion of the interventional device associated with the imaging device, wherein the imaging predictive model is configured with kinematics of the interventional device to receive the imaging data and to output the predicted navigated pose of the interventional device;
generating error positioning data derived from a differential aspect between a target pose of the portion of the interventional device associated with the imaging device and the predicted navigated pose of the portion of the interventional device associated with the imaging device, wherein the error positioning data comprises at least one velocity for the portion of the interventional device associated with the imaging device;
applying a control predictive model to the error positioning data to predict a corrective positioning motion of the interventional device, wherein the control predictive model configured with kinematics of the interventional device to receive the error positioning data and to output the predicted corrective positioning motion of the interventional device,
wherein the predicted corrective positioning motion comprises one or more joint velocities for at least one joint of the interventional device, the one or more joint velocities derived, by the control predictive model, based on the at least one velocity for the portion of the interventional device associated with the imaging device; and
generating positioning commands controlling a corrective positioning of the portion of the interventional device associated with the imaging device to the target pose based on the predicted corrective positioning motion of the interventional device.

18. The positioning method of claim 17, wherein the imaging predictive model includes:
a neural network having an input layer configured to input the imaging data generated by the imaging device, and an output layer configured to output at least one of a translation, a rotation, and a pivoting of the interventional device relative to a position of the interventional device in a reference image,
wherein the neural network is configured to infer the predicted navigated pose of the portion of the interventional device associated with the imaging device based on at least one of the translation, the rotation, and the pivoting of the interventional device.

19. The positioning method of claim 17, wherein the imaging predictive model includes:
a neural network having an input layer configured to input the imaging data generated by the imaging device, and an output layer configured to output at least one of a linear velocity and an angular velocity of interventional device relative to a position of the interventional device in a reference image,
wherein the neural network is configured to infer the predicted navigated pose of the portion of the interventional device associated with the imaging device based on the at least one of the linear velocity and the angular velocity of the interventional device.

20. The positioning method of claim 17, wherein the control predictive model includes:
a neural network having an input layer configured with the error positioning data derived from a differential motion between at least one of a linear velocity and an angular velocity of the portion of the interventional device associated with the imaging device and at least one of a predicted linear velocity and a predicted angular velocity of the portion of the interventional device associated with the imaging device, and an output layer configured to output the one or more joint velocities of the imaging device from a regression of the differential motion between the at least one of the linear velocity and the angular velocity and the at least one of the predicted linear velocity and the predicted angular velocity.

\* \* \* \* \*